(12) United States Patent
Blancher et al.

(10) Patent No.: US 9,637,538 B2
(45) Date of Patent: May 2, 2017

(54) ANTI-HLA MONOCLONAL CHIMERIC IMMUNOGLOBULIN, PROCESS AND KIT EMPLOYING SUCH A MONOCLONAL CHIMERIC IMMUNOGLOBULIN

(71) Applicants: UNIVERSITE PAUL SABATIER TOULOUSE III, Toulouse (FR); CENTRE HOSPITALIER UNIVERSITAIRE DE TOULOUSE, Toulouse (FR); CAYLA, Toulouse (FR)

(72) Inventors: Antoine Blancher, Toulouse (FR); Nicolas Congy, La Croix Falgarde (FR); Jean-Gerard Tiraby, Toulouse (FR); Daniel Drocourt, Toulouse (FR)

(73) Assignees: UNIVERSITE PAUL SABATIER TOULOUSE III, Toulouse (FR); CENTRE HOSPITALIER UNIVERSITAIRE DE TOULOUSE, Toulouse (FR); INVIVOGEN, Toulouse (FR)

( * ) Notice: Subject to any disclaimer, the term of this patent is extended or adjusted under 35 U.S.C. 154(b) by 892 days.

(21) Appl. No.: 13/869,477

(22) Filed: Apr. 24, 2013

(65) Prior Publication Data
US 2013/0288387 A1 Oct. 31, 2013

Related U.S. Application Data

(60) Provisional application No. 61/639,244, filed on Apr. 27, 2012.

(51) Int. Cl.
*C07K 16/28* (2006.01)
*C07K 16/18* (2006.01)
*G01N 33/68* (2006.01)
*G01N 33/569* (2006.01)

(52) U.S. Cl.
CPC .......... *C07K 16/18* (2013.01); *C07K 16/2833* (2013.01); *G01N 33/56977* (2013.01); *G01N 33/6893* (2013.01); *C07K 2317/24* (2013.01); *C07K 2317/34* (2013.01)

(58) Field of Classification Search
None
See application file for complete search history.

(56) References Cited

U.S. PATENT DOCUMENTS 6,750,321 B1 * 6/2004 Chen ...................... A61K 38/30
530/317
2005/0214852 A1 * 9/2005 Gaynor .................... C07K 7/06
435/6.11

FOREIGN PATENT DOCUMENTS

EP 1 927 367 A1 6/2008

OTHER PUBLICATIONS

Mekhaiel et al (Scientific Reports 1:124/DOI: 10.1038/srep00124, pp. 1-11).*
UniprotKB-P01834 (1986).*
ENA (2006, 1 page).*
Kosmac et al (DNA Fingerprinting, Sequencing and Chips, Chapter 3, 2009, Ed. Kresten Ovensen and Ulrich Matthiesen, Nova Science Publ., Inc.).*
M. Dechant: "Chimeric IgA antibodies against HLA class II effectively trigger lymphoma cell killing", Blood, vol. 100, No. 13, Dec. 15, 2002 (Dec. 15, 2802), pp. 4574-4580, XP55030869, ISSN: 0006-4971, 001: 18. 1182/blood-2002-83-8687 * figure 3.*.
K. Mizutani et al.: "The Importance of Anti-HLA-Specific Antibody Strength in Monitoring Kidney Transplant Patients", American Journal of Transplantation, vol. 7, No. 4, Apr. 1, 2007 (2087-84-01), pp. 1027-1031, XP55030268, ISSN: 1600-6135, DOI: 10.1111/j.1600-6143.2006.01721.x * p. 1028.*.
El-Awar et al.: "HLA Class I Epitopes: Recognition of Binding Sites by mAbs or Eluted Alloantibody Confirmed With Single Recombinant Antigens", Human Immunology, New York, NY, US, vol. 68, No. 3, Mar. 8, 2007 (2007-83-88), pp. 170-180, XP885917287, ISSN: 0198-8859, DOI: 10.1016/J.HUMIMM.2006.11.006 * p. 172 .*.
Barnstable CJ et al.: "Production of monoclonal antibodies to group A erythrocytes, HLA and other human cell surface antigens—new tools for genetic analysis", , Cell, vol. 14, 9-20, May 1978.
Ladasky JJ et al. "Residue 3 of beta2-microglobulin affects binding of class 1 MHC molecules by the W6132 antibody", (1999), Immunogenetics, 49(4), 312-320.
Elsasser, D. et al.: "HLA class II as potential target antigen on malignant B cells for therapy with bispecific antibodies in combination with granulocyte colony-stimulating factor", (1996), Blood, 87(9), 3803-3812, Blood, vol. 87, No. 9, May 1, 1996.

* cited by examiner

*Primary Examiner* — Gerald R Ewoldt
*Assistant Examiner* — Marianne Dibrino
(74) *Attorney, Agent, or Firm* — Young & Thompson

(57) ABSTRACT

A monoclonal chimeric immunoglobulin wherein the heavy chains and the light chains are human by nature in their constant parts, in particular, the heavy chain constant parts are chosen from the group formed of the heavy chain constant parts of an IgA, of an IgG or of an IgM and the light chain constant parts are chosen from the group formed of the kappa chains and the lambda chains, and the light chain and the heavy chain variable parts are chosen from the group formed of monoclonal antibodies specific to monomorphic epitopes of HLA class I antigens and monoclonal antibodies specific to monomorphic epitopes of HLA class II antigens. A process for standardization of the screening and for quantification of anti-HLA antibodies in a liquid medium is also described.

5 Claims, 14 Drawing Sheets

MetLysSerGlnThrGlnValPheValPhe
1
SerIleValMetThrGlnThrProLysPhe
21
IleThrCysLysAlaSerGlnSerValSer
41
GlyGlnSerProLysLeuLeuIleTyrTyr
61
ArgPheThrGlySerGlyTyrGlyThrAsp
81
GluAspLeuAlaValTyrPheCysGlnGln
101
GlyGlyThrLysLeuGluIleArgArgThr
121
ProSerAspGluGlnLeuLysSerGlyThr
141
TyrProArgGluAlaLysValGlnTrpLys
161
GlnGluSerValThrGluGlnAspSerLys
181
ThrLeuSerLysAlaAspTyrGluLysHis
201
GlyLeuSerSerProValThrLysSerPhe
221

LeuLeuLeuCysValSerGlyAlaHisGly
11
LeuLeuValSerAlaGlyAspArgValThr
31
AsnAspValAlaTrpTyrGlnGlnLysPro
51
AlaSerAsnArgTyrThrGlyValProAsp
71
PheThrPheThrIleSerThrValGlnAla
91
AspTyrSerSerProProTrpThrPheGly
111
ValAlaAlaProSerValPheIlePhePro
131
AlaSerValValCysLeuLeuAsnAsnPhe
151
ValAspAsnAlaLeuGlnSerGlyAsnSer
171
AspSerThrTyrSerLeuSerSerThrLeu
191
LysValTyrAlaCysGluValThrHisGln
211
AsnArgGlyGluCys
231

Fig 9

MetAlaValLeuValLeuLeuPheCysLeu
1
ValGlnLeuLysGlnSerGlyProGlyLeu
21
CysThrValSerGlyPheSerLeuThrSer
41
GlyLysGlyLeuGluTrpLeuGlyValIle
61
AlaPheIleSerArgLeuSerIleArgLys
81
MetAsnSerLeuGlnAlaAspAspThrAla
101
SerThrSerAlaTrpPheAlaTyrTrpGly
121
SerThrLysGlyProSerValPheProLeu
141
ThrAlaAlaLeuGlyCysLeuValLysAsp
161
AsnSerGlyAlaLeuThrSerGlyValHis
181
LeuTyrSerLeuSerSerValValThrVal
201
IleCysAsnValAsnHisLysProSerAsn
221
SerCysAspLysThrHisThrCysProPro
241
SerValPheLeuPheProProLysProLys
261
ValThrCysValValValAspValSerHis
281
ValAspGlyValGluValHisAsnAlaLys
301
ThrTyrArgValValSerValLeuThrVal
321
TyrLysCysLysValSerAsnLysAlaLeu
341
AlaLysGlyGlnProArgGluProGlnVal
361
ThrLysAsnGlnValSerLeuThrCysLeu
381
ValGluTrpGluSerAsnGlyGlnProGlu
401
AspSerAspGlySerPhePheLeuTyrSer
421
GlnGlyAsnValPheSerCysSerValMet
441
LysSerLeuSerLeuSerProGlyLys
461

ValThrPheProSerCysValLeuSerGln
11
ValGlnProSerGlnSerLeuSerLeuThr
31
TyrGlyValHisTrpValArgGlnProPro
51
TrpSerGlyGlySerThrAspTyrAsnAla
71
AspAsnSerLysSerGlnValPhePheLys
91
IleTyrTyrCysAlaArgThrPheThrThr
111
GlnGlyThrLeuValThrValSerAlaAla
131
AlaProSerSerLysSerThrSerGlyGly
151
TyrPheProGluProValThrValSerTrp
171
ThrPheProAlaValLeuGlnSerSerGly
191
ProSerSerSerLeuGlyThrGlnThrTyr
211
ThrLysValAspLysLysValGluProLys
231
CysProAlaProGluLeuLeuGlyGlyPro
251
AspThrLeuMetIleSerArgThrProGlu
271
GluAspProGluValLysPheAsnTrpTyr
291
ThrLysProArgGluGluGlnTyrAsnSer
311
LeuHisGlnAspTrpLeuAsnGlyLysGlu
331
ProAlaProIleGluLysThrIleSerLys
351
TyrThrLeuProProSerArgAspGluLeu
371
ValLysGlyPheTyrProSerAspIleAla
391
AsnAsnTyrLysThrThrProProValLeu
411
LysLeuThrValAspLysSerArgTrpGln
431
HisGluAlaLeuHisAsnHisTyrThrGln
451

Fig 10

MetAlaValLeuValLeuLeuPheCysLeu
1
ValGlnLeuLysGlnSerGlyProGlyLeu
21
CysThrValSerGlyPheSerLeuThrSer
41
GlyLysGlyLeuGluTrpLeuGlyValIle
61
AlaPheIleSerArgLeuSerIleArgLys
81
MetAsnSerLeuGlnAlaAspAspThrAla
101
SerThrSerAlaTrpPheAlaTyrTrpGly
121
SerProThrSerProLysValPheProLeu
141
ValValValAlaCysLeuValGlnGlyPhe
161
SerGluSerGlyGlnAsnValThrAlaArg
181
AspLeuTyrThrThrSerSerGlnLeuThr
201
SerValThrCysHisValLysHisTyrThr
221
ProValProProProProProCysCysHis
241
GluAspLeuLeuLeuGlySerGluAlaAsn
261
AlaSerGlyAlaThrPheThrTrpThrPro
281
ProGluArgAspLeuCysGlyCysTyrSer
301
ProTrpAsnHisGlyGluThrPheThrCys
321
LeuThrAlaAsnIleThrLysSerGlyAsn
341
ProProSerGluGluLeuAlaLeuAsnGlu
361
PheSerProLysAspValLeuValArgTrp
381
LysTyrLeuThrTrpAlaSerArgGlnGlu
401
ThrSerIleLeuArgValAlaAlaGluAsp
421
ValGlyHisGluAlaLeuProLeuAlaPhe
441
LysProThrHisValAsnValSerValVal
461

ValThrPheProSerCysValLeuSerGln
11
ValGlnProSerGlnSerLeuSerLeuThr
31
TyrGlyValHisTrpValArgGlnProPro
51
TrpSerGlyGlySerThrAspTyrAsnAla
71
AspAsnSerLysSerGlnValPhePheLys
91
IleTyrTyrCysAlaArgThrPheThrThr
111
GlnGlyThrLeuValThrValSerAlaAla
131
SerLeuAspSerThrProGlnAspGlyAsn
151
PheProGlnGluProLeuSerValThrTrp
171
AsnPheProProSerGlnAspAlaSerGly
191
LeuProAlaThrGlnCysProAspGlyLys
211
AsnProSerGlnAspValThrValProCys
231
ProArgLeuSerLeuHisArgProAlaLeu
251
LeuThrCysThrLeuThrGlyLeuArgAsp
271
SerSerGlyLysSerAlaValGlnGlyPro
291
ValSerSerValLeuProGlyCysAlaGln
311
ThrAlaAlaHisProGluLeuLysThrPro
331
ThrPheArgProGluValHisLeuLeuPro
351
LeuValThrLeuThrCysLeuAlaArgGly
371
LeuGlnGlySerGlnGluLeuProArgGlu
391
ProSerGlnGlyThrThrThrPheAlaVal
411
TrpLysLysGlyAspThrPheSerCysMet
431
ThrGlnLysThrIleAspArgLeuAlaGly
451
MetAlaGluValAspGlyThrCysTyr
471

Fig 11

| | |
|---|---|
| MetAlaValLeuValLeuLeuPheCysLeu 1 | ValThrPheProSerCysValLeuSerGln 11 |
| ValGlnLeuLysGlnSerGlyProGlyLeu 21 | ValGlnProSerGlnSerLeuSerLeuThr 31 |
| CysThrValSerGlyPheSerLeuThrSer 41 | TyrGlyValHisTrpValArgGlnProPro 51 |
| GlyLysGlyLeuGluTrpLeuGlyValIle 61 | TrpSerGlyGlySerThrAspTyrAsnAla 71 |
| AlaPheIleSerArgLeuSerIleArgLys 81 | AspAsnSerLysSerGlnValPhePheLys 91 |
| MetAsnSerLeuGlnAlaAspAspThrAla 101 | IleTyrTyrCysAlaArgThrPheThrThr 111 |
| SerThrSerAlaTrpPheAlaTyrTrpGly 121 | GlnGlyThrLeuValThrValSerAlaAla 131 |
| SerAlaProThrLeuPheProLeuValSer 141 | CysGluAsnSerProSerAspThrSerSer 151 |
| ValAlaValGlyCysLeuAlaGlnAspPhe 161 | LeuProAspSerIleThrPheSerTrpLys 171 |
| TyrLysAsnAsnSerAspIleSerSerThr 181 | ArgGlyPheProSerValLeuArgGlyGly 191 |
| LysTyrAlaAlaThrSerGlnValLeuLeu 201 | ProSerLysAspValMetGlnGlyThrAsp 211 |
| GluHisValValCysLysValGlnHisPro 221 | AsnGlyAsnLysGluLysAsnValProLeu 231 |
| ProValIleAlaGluLeuProProLysVal 241 | SerValPheValProProArgAspGlyPhe 251 |
| PheGlyAsnProArgLysSerLysLeuIle 261 | CysGlnAlaThrGlyPheSerProArgGln 271 |
| IleGlnValSerTrpLeuArgGluGlyLys 281 | GlnValGlySerGlyValThrThrAspGln 291 |
| ValGlnAlaGluAlaLysGluSerGlyPro 301 | ThrThrTyrLysValThrSerThrLeuThr 311 |
| IleLysGluSerAspTrpLeuSerGlnSer 321 | MetPheThrCysArgValAspHisArgGly 331 |
| LeuThrPheGlnGlnAsnAlaSerSerMet 341 | CysValProAspGlnAspThrAlaIleArg 351 |
| ValPheAlaIleProProSerPheAlaSer 361 | IlePheLeuThrLysSerThrLysLeuThr 371 |
| CysLeuValThrAspLeuThrThrTyrAsp 381 | SerValThrIleSerTrpThrArgGlnAsn 391 |
| GlyGluAlaValLysThrHisThrAsnIle 401 | SerGluSerHisProAsnAlaThrPheSer 411 |
| AlaValGlyGluAlaSerIleCysGluAsp 421 | AspTrpAsnSerGlyGluArgPheThrCys 431 |
| ThrValThrHisThrAspLeuProSerPro 441 | LeuLysGlnThrIleSerArgProLysGly 451 |
| ValAlaLeuHisArgProAspValTyrLeu 461 | LeuProProAlaArgGluGlnLeuAsnLeu 471 |
| ArgGluSerAlaThrIleThrCysLeuVal 481 | ThrGlyPheSerProAlaAspValPheVal 491 |
| GlnTrpMetGlnArgGlyGlnProLeuSer 501 | ProGluLysTyrValThrSerAlaProMet 511 |
| ProGluProGlnAlaProGlyArgTyrPhe 521 | AlaHisSerIleLeuThrValSerGluGlu 531 |
| GluTrpAsnThrGlyGluThrTyrThrCys 541 | ValValAlaHisGluAlaLeuProAsnArg 551 |
| ValThrGluArgThrValAspLysSerThr 561 | GlyLysProThrLeuTyrAsnValSerLeu 571 |
| ValMetSerAspThrAlaGlyThrCysTyr 581 | |

Fig 12

MetAspPheGlnValGlnIlePheSerPhe
1
ArgGlyGlnIleValLeuThrGlnSerPro
21
ValThrMetThrCysSerAlaSerSerIle
41
ProGlySerSerProArgLeuLeuIleTyr
61
ValArgPheSerGlySerGlySerGlyThr
81
AlaGluAspAlaAlaThrTyrPheCysGln
101
GlyGlyThrLysLeuGluIleLysArgThr
121
ProSerAspGluGlnLeuLysSerGlyThr
141
TyrProArgGluAlaLysValGlnTrpLys
161
GlnGluSerValThrGluGlnAspSerLys
181
ThrLeuSerLysAlaAspTyrGluLysHis
201
GlyLeuSerSerProValThrLysSerPhe
221

LeuLeuIleSerAlaSerValIleLeuSer
11
AlaIleMetSerAlaSerProGlyGluLys
31
ValArgTyrMetTyrTrpPheGlnGlnLys
51
AspThrSerSerLeuSerSerGlyValPro
71
SerTyrSerLeuThrIleSerArgMetGlu
91
GlnTrpSerSerTyrProLeuThrPheGly
111
ValAlaAlaProSerValPheIlePhePro
131
AlaSerValValCysLeuLeuAsnAsnPhe
151
ValAspAsnAlaLeuGlnSerGlyAsnSer
171
AspSerThrTyrSerLeuSerSerThrLeu
191
LysValTyrAlaCysGluValThrHisGln
211
AsnArgGlyGluCys
231

Fig 13

MetAspLeuArgLeuSerCysAlaPheIle
1
ValLysLeuGluGluSerGlyGlyGlyLeu
21
CysValAlaSerGlyPheThrPheSerAsn
41
GluLysGlyLeuGluTrpValAlaGluIle
61
TyrAlaGluSerValLysGlyArgPheThr
81
TyrLeuGlnMetAsnAsnLeuArgSerGlu
101
SerTyrSerPheAspTyrTrpGlyGlnGly
121
ThrSerProLysValPheProLeuSerLeu
141
ValAlaCysLeuValGlnGlyPhePhePro
161
SerGlyGlnAsnValThrAlaArgAsnPhe
181
TyrThrThrSerSerGlnLeuThrLeuPro
201
ThrCysHisValLysHisTyrThrAsnPro
221
ProProProProProCysCysHisProArg
241
LeuLeuLeuGlySerGluAlaAsnLeuThr
261
GlyAlaThrPheThrTrpThrProSerSer
281
ArgAspLeuCysGlyCysTyrSerValSer
301
AsnHisGlyGluThrPheThrCysThrAla
321
AlaAsnIleThrLysSerGlyAsnThrPhe
341
SerGluGluLeuAlaLeuAsnGluLeuVal
361
ProLysAspValLeuValArgTrpLeuGln
381
LeuThrTrpAlaSerArgGlnGluProSer
401
IleLeuArgValAlaAlaGluAspTrpLys
421
HisGluAlaLeuProLeuAlaPheThrGln
441
ThrHisValAsnValSerValValMetAla
461

IleValLeuLeuLysGlyValGlnSerGlu
11
ValGlnProGlyGlySerMetLysLeuSer
31
SerTrpMetAsnTrpValArgGlnSerPro
51
ArgLeuLysSerAsnAsnTyrAlaThrArg
71
IleSerArgAspAspSerLysSerSerVal
91
AspThrAlaIleTyrTyrCysThrProLeu
111
ThrThrValThrValSerThrAlaSerPro
131
AspSerThrProGlnAspGlyAsnValVal
151
GlnGluProLeuSerValThrTrpSerGlu
171
ProProSerGlnAspAlaSerGlyAspLeu
191
AlaThrGlnCysProAspGlyLysSerVal
211
SerGlnAspValThrValProCysProVal
231
LeuSerLeuHisArgProAlaLeuGluAsp
251
CysThrLeuThrGlyLeuArgAspAlaSer
271
GlyLysSerAlaValGlnGlyProProGlu
291
SerValLeuProGlyCysAlaGlnProTrp
311
AlaHisProGluLeuLysThrProLeuThr
331
ArgProGluValHisLeuLeuProProPro
351
ThrLeuThrCysLeuAlaArgGlyPheSer
371
GlySerGlnGluLeuProArgGluLysTyr
391
GlnGlyThrThrThrPheAlaValThrSer
411
LysGlyAspThrPheSerCysMetValGly
431
LysThrIleAspArgLeuAlaGlyLysPro
451
GluValAspGlyThrCysTyr
471

Fig 14

| | |
|---|---|
| MetAspLeuArgLeuSerCysAlaPheIle 1 | IleValLeuLeuLysGlyValGlnSerGlu 11 |
| ValLysLeuGluGluSerGlyGlyGlyLeu 21 | ValGlnProGlyGlySerMetLysLeuSer 31 |
| CysValAlaSerGlyPheThrPheSerAsn 41 | SerTrpMetAsnTrpValArgGlnSerPro 51 |
| GluLysGlyLeuGluTrpValAlaGluIle 61 | ArgLeuLysSerAsnAsnTyrAlaThrArg 71 |
| TyrAlaGluSerValLysGlyArgPheThr 81 | IleSerArgAspAspSerLysSerSerVal 91 |
| TyrLeuGlnMetAsnAsnLeuArgSerGlu 101 | AspThrAlaIleTyrTyrCysThrProLeu 111 |
| SerTyrSerPheAspTyrTrpGlyGlnGly 121 | ThrThrValThrValSerThrAlaSerThr 131 |
| LysGlyProSerValPheProLeuAlaPro 141 | SerSerLysSerThrSerGlyGlyThrAla 151 |
| AlaLeuGlyCysLeuValLysAspTyrPhe 161 | ProGluProValThrValSerTrpAsnSer 171 |
| GlyAlaLeuThrSerGlyValHisThrPhe 181 | ProAlaValLeuGlnSerSerGlyLeuTyr 191 |
| SerLeuSerSerValValThrValProSer 201 | SerSerLeuGlyThrGlnThrTyrIleCys 211 |
| AsnValAsnHisLysProSerAsnThrLys 221 | ValAspLysLysValGluProLysSerCys 231 |
| AspLysThrHisThrCysProProCysPro 241 | AlaProGluLeuLeuGlyGlyProSerVal 251 |
| PheLeuPheProProLysProLysAspThr 261 | LeuMetIleSerArgThrProGluValThr 271 |
| CysValValValAspValSerHisGluAsp 281 | ProGluValLysPheAsnTrpTyrValAsp 291 |
| GlyValGluValHisAsnAlaLysThrLys 301 | ProArgGluGluGlnTyrAsnSerThrTyr 311 |
| ArgValValSerValLeuThrValLeuHis 321 | GlnAspTrpLeuAsnGlyLysGluTyrLys 331 |
| CysLysValSerAsnLysAlaLeuProAla 341 | ProIleGluLysThrIleSerLysAlaLys 351 |
| GlyGlnProArgGluProGlnValTyrThr 361 | LeuProProSerArgGluGluMetThrLys 371 |
| AsnGlnValSerLeuThrCysLeuValLys 381 | GlyPheTyrProSerAspIleAlaValGlu 391 |
| TrpGluSerAsnGlyGlnProGluAsnAsn 401 | TyrLysThrThrProProValLeuAspSer 411 |
| AspGlySerPhePheLeuTyrSerLysLeu 421 | ThrValAspLysSerArgTrpGlnGlnGly 431 |
| AsnValPheSerCysSerValMetHisGlu 441 | AlaLeuHisAsnHisTyrThrGlnLysSer 451 |
| LeuSerLeuSerProGlyLys 461 | |

Fig 15

1 MetAspLeuArgLeuSerCysAlaPheIle
11 IleValLeuLeuLysGlyValGlnSerGlu
21 ValLysLeuGluGluSerGlyGlyGlyLeu
31 ValGlnProGlyGlySerMetLysLeuSer
41 CysValAlaSerGlyPheThrPheSerAsn
51 SerTrpMetAsnTrpValArgGlnSerPro
61 GluLysGlyLeuGluTrpValAlaGluIle
71 ArgLeuLysSerAsnAsnTyrAlaThrArg
81 TyrAlaGluSerValLysGlyArgPheThr
91 IleSerArgAspAspSerLysSerSerVal
101 TyrLeuGlnMetAsnAsnLeuArgSerGlu
111 AspThrAlaIleTyrTyrCysThrProLeu
121 SerTyrSerPheAspTyrTrpGlyGlnGly
131 ThrThrValThrValSerThrAlaSerAla
141 ProThrLeuPheProLeuValSerCysGlu
151 AsnSerProSerAspThrSerSerValAla
161 ValGlyCysLeuAlaGlnAspPheLeuPro
171 AspSerIleThrPheSerTrpLysTyrLys
181 AsnAsnSerAspIleSerSerThrArgGly
191 PheProSerValLeuArgGlyGlyLysTyr
201 AlaAlaThrSerGlnValLeuLeuProSer
211 LysAspValMetGlnGlyThrAspGluHis
221 ValValCysLysValGlnHisProAsnGly
231 AsnLysGluLysAsnValProLeuProVal
241 IleAlaGluLeuProProLysValSerVal
251 PheValProProArgAspGlyPhePheGly
261 AsnProArgLysSerLysLeuIleCysGln
271 AlaThrGlyPheSerProArgGlnIleGln
281 ValSerTrpLeuArgGluGlyLysGlnVal
291 GlySerGlyValThrThrAspGlnValGln
301 AlaGluAlaLysGluSerGlyProThrThr
311 TyrLysValThrSerThrLeuThrIleLys
321 GluSerAspTrpLeuSerGlnSerMetPhe
331 ThrCysArgValAspHisArgGlyLeuThr
341 PheGlnGlnAsnAlaSerSerMetCysVal
351 ProAspGlnAspThrAlaIleArgValPhe
361 AlaIleProProSerPheAlaSerIlePhe
371 LeuThrLysSerThrLysLeuThrCysLeu
381 ValThrAspLeuThrThrTyrAspSerVal
391 ThrIleSerTrpThrArgGlnAsnGlyGlu
401 AlaValLysThrHisThrAsnIleSerGlu
411 SerHisProAsnAlaThrPheSerAlaVal
421 GlyGluAlaSerIleCysGluAspAspTrp
431 AsnSerGlyGluArgPheThrCysThrVal
441 ThrHisThrAspLeuProSerProLeuLys
451 GlnThrIleSerArgProLysGlyValAla
461 LeuHisArgProAspValTyrLeuLeuPro
471 ProAlaArgGluGlnLeuAsnLeuArgGlu
481 SerAlaThrIleThrCysLeuValThrGly
491 PheSerProAlaAspValPheValGlnTrp
501 MetGlnArgGlyGlnProLeuSerProGlu
511 LysTyrValThrSerAlaProMetProGlu
521 ProGlnAlaProGlyArgTyrPheAlaHis
531 SerIleLeuThrValSerGluGluGluTrp
541 AsnThrGlyGluThrTyrThrCysValVal
551 AlaHisGluAlaLeuProAsnArgValThr
561 GluArgThrValAspLysSerThrGlyLys
571 ProThrLeuTyrAsnValSerLeuValMet
581 SerAspThrAlaGlyThrCysTyr

Fig 16

ANTI-HLA MONOCLONAL CHIMERIC IMMUNOGLOBULIN, PROCESS AND KIT EMPLOYING SUCH A MONOCLONAL CHIMERIC IMMUNOGLOBULIN

FIELD OF THE INVENTION

The invention relates to an anti-HLA class I or anti-HLA class II monoclonal chimeric immunoglobulin. The invention relates in particular to such a monoclonal chimeric immunoglobulin which is suitable for use especially as a standardisation reagent for the screening and quantification of anti-HLA antibodies in a liquid medium, especially in a biological liquid medium. The invention relates in particular to such a monoclonal chimeric immunoglobulin having on the one hand the function of a monoclonal antibody and on the other hand a chimeric structure. The invention relates also to a standardised process for the screening of anti-HLA antibodies in a liquid medium and to a process for the quantification of anti-HLA antibodies in a liquid medium, in which processes such a monoclonal chimeric immunoglobulin is used. In particular, the invention relates to such a process for the quantification of anti-HLA antibodies in the serum of a patient, especially of a transplant patient or a patient awaiting a transplant.

The invention relates further to a diagnostic kit for carrying out such a process. In particular, the invention relates to such a process and such a diagnostic kit which are suitable for permitting accurate, reliable and rapid quantification of anti-HLA antibodies in a liquid medium, especially in a biological fluid collected from a patient.

BACKGROUND OF THE INVENTION

In the field of organ transplantation, it has been known since the 1930s that compatibility between the donor's tissue type, as defined by the HLA (Human Leucocyte Antigen) antigens, and the recipient's immune system, especially the antibodies, is essential to the success of the organ transplant.

The HLA antigens are carried by two types of membrane proteins which are highly immunogenic: HLA class I molecules and HLA class II molecules. Accordingly, the exposure of an individual to HLA alloantigens, that is to say antigens that are foreign and different from his own, can lead to the development of an immune response to those antigens. This immune response can be cell-mediated (alloreactive T lymphocytes) or humoral (synthesis of anti-HLA antibodies).

HLA class I antigens are coded for by three genes HLA-A, HLA-B and HLA-C, the polymorphism of which is responsible for the three series of alleles HLA-A, HLA-B and HLA-C, respectively. HLA class II antigens are coded for by the genes HLA-DP, HLA-DQ and HLA-DR.

In organ transplantation, it is crucial to minimise—or even eliminate—the risks of proposing to a patient awaiting a transplant an organ for transplant that expresses HLA antigens against which the patient is already immunised. In this situation, the risk of the occurrence of hyperacute humoral rejection—that is to say humoral rejection within a period of less than 24 hours following the transplant—is considerable. In addition, within the context of transplant monitoring, the early screening of the appearance in the transplant recipient patient of antibodies directed against the antigens of the transplanted organ allows said transplant recipient patient to be treated as early as possible in an attempt to control the development of the humoral response, which may result in the destruction of the transplant.

Monitoring of the alloimmunisation of both transplant patients and patients awaiting a transplant is therefore essential in order to ensure the survival of the transplants and of the transplant patients.

Within this context, it is necessary to be able to detect, identify and quantify anti-HLA antibodies in patients awaiting a transplant and in transplant patients. Numerous techniques for detecting anti-HLA antibodies have already been developed.

There is known in particular the technique called "complement-dependent microlymphocytotoxicity". This technique consists in presenting the serum of a patient, especially of a transplant recipient, to a series of cells of known HLA typing in the presence of rabbit complement. If antibodies (Ab) specific to the HLA antigens carried by the cells are present in the tested serum, and if those antibodies are capable of activating the complement (antibodies of class IgM and of subclass IgG-1 and IgG-3), complement-dependent cell lysis (CDC, Complement Dependent Cytotoxicity) reveals the presence of the antibodies. By virtue of a panel of cells expressing different HLA antigens, it is thus possible to screen the antibodies and then identify their specificity/specificities. This reference technique permits the detection of cytolytic anti-HLA antibodies, which are the most dangerous for the transplanted organ. However, this technique has low sensitivity in comparison with more recent techniques. This technique, which requires either the availability of a large variety of lymphocytes from donors of known HLA phenotype or the in vitro cultivation of a large number of HLA-typed cell lines, is therefore complex and laborious to carry out.

More sensitive techniques are also known, such as immunoenzymatic assay on a solid substrate ("ELISA" for "Enzyme-Linked ImmunoSorbent Assay"). In addition, there has recently appeared the technique of immunofluorimetry coupled with detection in flow, which is designed on the principle of flow cytometry. The principle of flow immunofluorimetry consists in fixing purified HLA class I or HLA class II antigens to the surface of polystyrene beads. The anti-HLA antibodies which recognise the HLA class I or HLA class II antigens bind to the antigens bound to the surface of the beads and are revealed by anti-IgG secondary antibodies coupled to a fluorescent group after washing of the polystyrene beads. The secondary antibodies are detected by flow fluorimetry. Their fluorescence intensity is additionally quantified.

For screening tests there is used a plurality of types of beads in admixture, each type of beads carrying on the surface a plurality of HLA antigens, either of class I or of class II. Such an approach allows the presence of anti-HLA antibodies to be detected but without permitting the identification of their specificity/specificities.

In order to identify and characterise the specificity of the antibody, on the other hand, there is used a plurality of types of beads in admixture, each type of beads carrying on the surface a single HLA antigen.

Kits for the detection and identification of anti-HLA antibodies are known. They comprise polystyrene beads coated with HLA class I antigens or HLA class II antigens, and polystyrene beads coated with human IgGs. Also marketed are an anti-human IgG secondary antibody coupled to phycoerythrin, and a serum without anti-HLA antibodies as negative control. Such a negative control is suitable for quantifying the non-specific fixing of the secondary antibody to the polystyrene beads. Such kits do not comprise a positive control, or a sensitivity control, or a standard allowing the concentration of anti-HLA antibodies (expressed, for example, in mole/l or in g/l) in the analysed medium to be derived precisely from the measured fluorescence intensity.

In addition, such kits without a calibration and/or sensitivity control do not allow the sensitivity threshold of the analysis method to be determined, that is to say the minimum value of the signal that makes it possible to affirm that the signal observed is significantly greater than the background noise of the measurement.

In order to remedy this lack of a positive control in methods for the screening and/or quantification of anti-HLA antibodies, immunology and histocompatibility laboratories use, as positive control, a mixture of several serums of several individuals immunised against several HLA antigens.

In such a positive control, the concentration of each of the antibodies of the serums of the immunised individuals is unknown. Such a mixture of serums does not allow the intensity of the fluorescence measurement to be correlated with a concentration (mol/l or g/l) of a specific antibody of the mixture of serums. It therefore does not allow the antibodies present in the serum of the transplant patient or patient awaiting transplant to be quantified. It therefore also does not allow the real risks of the occurrence of a hyper-acute humoral response to be evaluated.

The reactivity of such a mixture of serums is variable from one antigen to another, and their use does not allow the detection threshold to be fixed for each HLA antigen studied. Moreover, such a mixture of polyclonal antibodies obtained from patient serums is available in a limited quantity and is quickly exhausted. It must therefore be replaced by a different mixture, which is also available in a variable quantity, which does not allow said mixture to be exchanged between laboratories with a view to standardisation of the results. The variability of the mixtures of serums from one batch to another requires frequent validation of the batches, which are neither comparable nor reproducible from one batch to another.

Using such a mixture of serums, the inventors have shown (FIGS. 2, 3 and 4) that the fluorescence intensity value associated with each type of polystyrene beads depends on the nature of the HLA class I or class II antigen carried by each of the types of polystyrene beads. In addition, the fluorescence intensity value associated with each of the types of polystyrene beads shows considerable variability over time, especially over a period of approximately five months. That value varies (FIG. 4, hatched histograms) between 1000 and 20,000 average fluorescence units.

As a result, the average value of the fluorescence intensity measured on all the polystyrene beads exhibits a considerable dispersion (calculated by its standard deviation), which does not allow the anti-HLA antibodies in the liquid medium to be quantified. Such a dispersion is shown in FIG. 4 (hatched histograms) of the present patent application, which is given to illustrate a standard of the prior art.

Such a dispersion of the fluorescence intensity measurements does not allow a distinction to be made (in particular for low fluorescence intensity values) between a fluorescence intensity value which is low but reflects the presence of a low concentration of anti-HLA antibodies, and a low fluorescence intensity value which cannot be distinguished from the background noise of the measurement.

For the same reasons as set out above, such a preparation used as a positive control in the prior art does not allow the concentration of antibodies present in the liquid medium, especially in a serum collected from a transplant patient or a patient awaiting a transplant, to be determined precisely.

The invention aims to remedy these disadvantages by proposing a monoclonal chimeric immunoglobulin as a standardisation and positive control and sensitivity reagent in the serological analysis of anti-HLA class I antibodies or anti-HLA class II antibodies, especially within the context of organ transplantation.

SUMMARY OF THE INVENTION

The invention aims to remedy the disadvantages discussed above by proposing a monoclonal chimeric immunoglobulin which is suitable for permitting reliable quantification of anti-HLA antibodies in the serum of a patient. Such a monoclonal chimeric immunoglobulin is suitable in particular for permitting the detection of the occurrence in a patient of antibodies directed against the antigens of the transplanted organ, even for a very low concentration of that antibody.

The invention aims to propose a monoclonal chimeric immunoglobulin which is suitable for the standardisation of anti-HLA antibody detection methods. By allowing in particular the detection threshold to be defined precisely, the monoclonal chimeric immunoglobulin according to the invention allows the biologist to validate the antibody detection method.

The invention aims to propose a monoclonal chimeric immunoglobulin which is suitable for permitting the detection as early as possible of the occurrence of anti-HLA antibodies directed against the HLA antigens of the transplanted organ. Such early detection in particular allows humoral rejection to be discovered as quickly as possible and therefore enables the curative treatment for rejection of the transplanted organ to be prescribed quickly.

The invention aims to propose such a monoclonal chimeric immunoglobulin which allows methods for the detection of anti-HLA antibodies in a biological liquid to be standardised and calibrated.

The invention aims also to propose such a monoclonal chimeric immunoglobulin which is capable of permitting the accreditation of a standardised method for the screening, quantification and characterisation of anti-HLA antibodies according to the new regulatory standards for accreditation of medical analysis laboratories. In France, medical analysis—especially immunology—laboratories must comply with COFRAC (French accreditation committee) standard 15189.

The invention aims also to propose a composition of at least one monoclonal chimeric immunoglobulin as quantitative calibration reagent in tests for screening anti-HLA antibodies, especially by immunofluorimetry.

The invention aims in particular to propose such a composition of at least one monoclonal chimeric immunoglobulin as quantification standard in tests for screening anti-HLA antibodies by "Luminex®" technology.

The invention aims also to propose such a composition of at least one chimeric immunoglobulin as quantitative standard in tests for screening anti-HLA antibodies by flow cytometry, by the ELISA technique or by complement-dependent microlymphocytotoxicity.

The invention therefore aims to propose such a monoclonal chimeric immunoglobulin and such a composition of at least one monoclonal chimeric immunoglobulin for use as quantitative standard instead of a complex mixture of antibodies obtained from the mixture of one or more serums of patients.

The invention aims also to propose such a monoclonal chimeric immunoglobulin which is available in a large quantity and the production of which is perfectly standardised in terms of anti-HLA antibody concentration and in terms of composition.

The invention aims in addition to propose a stable aqueous solution of such a monoclonal chimeric immunoglobulin, the concentration of monoclonal chimeric immunoglobulin of which is known perfectly, for the standardisation of a method for the screening and/or quantification and/or characterisation of anti-HLA antibodies in a liquid medium.

To that end, the invention relates to a monoclonal chimeric immunoglobulin formed of:
two polypeptide chains, called heavy chains (H), of molecular weight from 40 kDa to 60 kDa, and
two polypeptide chains, called light chains (L), of molecular weight from 20 kDa to 30 kDa,
wherein
each heavy chain (H) comprises:
a heavy chain variable region ($V_H$) of a monoclonal antibody chosen from the group formed of monoclonal antibodies specific to monomorphic epitopes of HLA class I antigens and monoclonal antibodies specific to monomorphic epitopes of HLA class II antigens, and
a heavy chain constant region ($C_H$) of a human immunoglobulin chosen from the group formed of IgAs, IgGs and IgMs,
and in that
each light chain (L) comprises:
a light chain variable region ($V_L$) of a monoclonal antibody chosen from the group formed of monoclonal antibodies specific to monomorphic epitopes of HLA class I antigens and monoclonal antibodies specific to monomorphic epitopes of HLA class II antigens, and
a light chain constant region ($C_L$) of a human immunoglobulin chosen from the group formed of the kappa chains and the lambda chains.

In the following, the expressions "HLA class I antigen" and "HLA class II antigen" (HLA for "Human Leucocyte Antigen") denote antigens which are human by nature.

Advantageously, a monoclonal antibody specific to a monomorphic epitope of HLA class I antigens is formed to be able to recognise an epitope common to all HLA class I antigens. Advantageously, a monoclonal antibody specific to a monomorphic epitope of anti-HLA class II antigens is formed to be able to recognise an epitope common to substantially all HLA class II antigens.

Advantageously, a monoclonal chimeric immunoglobulin according to the invention denotes an immunoglobulin in which:
the heavy chains and the light chains are human by nature in their constant parts. In particular, the heavy chain constant parts are chosen from the group formed of the heavy chain constant parts of an IgA, the heavy chain constant parts of an IgG and the heavy chain constant parts of an IgM, and the light chain constant parts are chosen from the group formed of the kappa chains and the lambda chains, and
the light chain and heavy chain variable parts are chosen from the group formed of monoclonal antibodies specific to monomorphic epitopes of HLA class I antigens and monoclonal antibodies specific to monomorphic epitopes of HLA class II antigens. In such a monoclonal chimeric immunoglobulin, the heavy chain constant parts ($C_H$) of the human antibody and the light chain constant parts ($C_L$) of the human antibody together represent approximately 60% by mass of the monoclonal chimeric immunoglobulin. In addition, such a monoclonal chimeric immunoglobulin is a monoclonal antibody, that is to say specific to a single monomorphic epitope.

Advantageously, the monoclonal chimeric immunoglobulin according to the invention is formed of two heavy chains (H) and two light chains (L), wherein:
each heavy chain (H) is formed of:
a heavy chain variable region ($V_H$) of a monoclonal antibody chosen from the group formed of monoclonal antibodies specific to monomorphic epitopes of HLA class I antigens and monoclonal antibodies specific to monomorphic epitopes of HLA class II antigens, and
a heavy chain constant region ($C_H$) of a human immunoglobulin chosen from the group formed of IgAs, IgGs and IgMs,
and in that:
each light chain (L) is formed of:
a light chain variable region ($V_L$) of a monoclonal antibody chosen from the group formed of monoclonal antibodies specific to monomorphic epitopes of HLA class I antigens and monoclonal antibodies specific to monomorphic epitopes of HLA class II antigens, and
a light chain constant region ($C_L$) of a human immunoglobulin chosen from the group formed of the kappa chains and the lamba chains.

Advantageously, each monoclonal antibody is chosen from the group formed of the monoclonal antibodies of a vertebrate organism, especially a non-human vertebrate organism, specific to monomorphic epitopes of HLA class I antigens and the monoclonal antibodies of a vertebrate organism, especially a non-human vertebrate organism, specific to monomorphic epitopes of HLA class II antigens.

In the following, "non-human vertebrate organism" is understood as being a superior organised living being with the exception of a human. Such a vertebrate organism is in particular provided with an immune system. Such a vertebrate organism is in particular chosen from the group formed of non-human mammals, especially a mouse, a rat, a rabbit and a hamster, an amphibian and a bird, especially galliformes. Such non-human vertebrate organisms are in particular laboratory animals. However, such a monoclonal antibody can be chosen from the group formed of human monoclonal antibodies.

Advantageously and according to the invention, each monoclonal antibody specific to monomorphic epitopes of HLA class I antigens and each monoclonal antibody specific to monomorphic epitopes of HLA class II antigens is chosen from the group formed of the monoclonal antibodies of a vertebrate, in particular the monoclonal antibodies of a mammal, especially of a mouse, rat, rabbit, hamster and of a human, and the monoclonal antibodies of a non-mammalian vertebrate, especially of an amphibian, of a bird, in particular of a galliforme.

Advantageously and according to the invention, the monoclonal antibody specific to monomorphic epitopes of HLA class I antigens is the W6/32 antibody.

Advantageously and according to the invention, the monoclonal antibody specific to monomorphic epitopes of HLA class II antigens is the F.3.3 antibody.

The invention relates in addition to a stable solution of at least one monoclonal chimeric immunoglobulin according to the invention in an aqueous composition.

The invention relates also to such an aqueous solution of at least one monoclonal chimeric immunoglobulin according to the invention, said aqueous solution having a predetermined concentration of said monoclonal chimeric immunoglobulin.

The invention relates also to such a monoclonal chimeric immunoglobulin which is suitable for permitting a determination of the quantity of anti-HLA antibody in a liquid medium containing antibodies.

The invention relates also to the use of such a monoclonal chimeric immunoglobulin for the screening and quantification of anti-HLA antibodies in a liquid medium.

The invention relates in particular to the use of a monoclonal chimeric immunoglobulin according to the invention in a screening method, especially a method for the detection or a method for the identification or quantification of anti-HLA antibodies chosen from the group formed of multiplex quantitative immunofluorimetry methods, flow cytometry methods, methods of immunoenzymatic assay on a solid substrate (ELISA) and complement-dependent microlymphocytotoxicity methods.

In particular, there is used a monoclonal chimeric immunoglobulin according to the invention in which the heavy chain constant parts ($C_H$) and the light chain constant parts ($C_L$) are constituted by the constant parts of a human IgA in competition tests. Such class IgA monoclonal chimeric immunoglobulins according to the invention are suitable for inhibiting at least partially the fixing of anti-HLA class IgG (or IgM) polyclonal antibodies present in the serum of the patients. The inhibition of the fixing of the IgGs of the serum by the class IgA monoclonal chimeric immunoglobulins according to the invention makes it possible to demonstrate the specificity of the fixing of the IgGs to the immunoadsorbent substrates used in the tests for screening anti-HLA antibodies by multiplex quantitative immunofluorimetry with reading in flow on a "Luminex®" apparatus, by flow cytometry, by ELISA techniques, and by complement-dependent microlymphocytotoxicity.

In particular, the class IgA monoclonal chimeric immunoglobulins make it possible to differentiate a specific signal corresponding to the actual presence of anti-HLA IgG in the serum from a non-specific signal corresponding to the adsorption of the IgGs on the substrate having HLA antigens. This competition of the class IgA monoclonal chimeric immunoglobulins according to the invention for the detection of anti-HLA IgG has been demonstrated by quantitative immunofluorimetry on Luminex®.

The class IgG and class IgM monoclonal chimeric immunoglobulins according to the invention can be used as positive controls and sensitivity controls for direct compatibility testing (cross-match) between a recipient and an organ donor carried out just before the organ transplant by any suitable technique (complement-dependent microlymphocytotoxicity or flow cytometry) and in any technique for detection of class IgG or IgM antibodies on an immunoabsorbent substrate (ELISA or quantitative immunofluorimetry on polystyrene beads).

The invention relates also to a process for the determination of the quantity of anti-HLA antibodies in a liquid medium containing antibodies, wherein:
  a plurality of solutions ($S_n$), especially aqueous solutions, of a monoclonal chimeric immunoglobulin is prepared, each solution ($S_n$) having a defined concentration value ($C_n$) of said monoclonal chimeric immunoglobulin, and then
  each solution ($S_n$) is placed in contact with the same defined quantity of at least one immobilised HLA antigen, and a calibration curve is produced, in which each defined concentration value ($C_n$) is associated with a measured value ($V_n$) of a parameter, said measured value ($V_n$) representing a quantity ($Q_n$) of the monoclonal chimeric immunoglobulin bound to the defined quantity of each immobilised HLA antigen, in which process the monoclonal chimeric immunoglobulin is formed of:
  two polypeptide chains, called heavy chains (H), of molecular weight from 40 kDa to 60 kDa, and
  two polypeptide chains, called light chains (L), of molecular weight from 20 kDa to 30 kDa,
wherein:
each heavy chain (H) comprises:
  a heavy chain variable region ($V_H$) of a monoclonal antibody chosen from the group formed of monoclonal antibodies specific to monomorphic epitopes of HLA class I antigens and monoclonal antibodies specific to monomorphic epitopes of HLA class II antigens, and
  a heavy chain constant region ($C_H$) of a human immunoglobulin chosen from the group formed of IgAs, IgGs and IgMs,
and in that
each light chain (L) comprises:
  a light chain variable region ($V_L$) of a monoclonal antibody chosen from the group formed of monoclonal antibodies specific to monomorphic epitopes of HLA class I antigens and monoclonal antibodies specific to monomorphic epitopes of HLA class II antigens, and
  a light chain constant region ($C_L$) of a human immunoglobulin chosen from the group formed of the kappa chains and the lambda chains.

The invention therefore consists also in proposing a process for the in vitro quantification of anti-HLA antibodies, wherein a calibration curve is produced from a solution of at least one monoclonal chimeric immunoglobulin according to the invention, said monoclonal chimeric immunoglobulin having a known concentration in said solution.

The inventors have in fact found that no solution is known in the prior art for permitting a reliable and reproducible quantitative evaluation of the concentration of anti-HLA class I and class II antibodies in a liquid medium.

Advantageously and according to the invention, the parameter is chosen from the group formed of fluorescence parameters, luminescence parameters and colorimetry parameters.

Advantageously and according to the invention, the defined concentration ($C_x$) of monoclonal chimeric immunoglobulin is from $10^{-10}$ g/ml to $10^{-4}$ g/ml.

Advantageously and according to the invention, in order to produce the calibration curve:
  there is formed, from pairs ($C_n$, $V_n$) of defined concentration ($C_n$) and measured value ($V_n$), the calibration curve showing the variation of the measured value ($V_n$) as a function of the defined concentration ($C_n$) of monoclonal chimeric immunoglobulin of each solution ($S_n$) of monoclonal chimeric immunoglobulin, and
  there is calculated a value, called a threshold value, of the fluorescence parameter beyond which the concentration of monoclonal chimeric immunoglobulin is significantly greater than 0.

Advantageously, increasing progressive dilutions of the monoclonal chimeric immunoglobulin according to the invention are prepared. These solutions ($S_n$) of monoclonal chimeric immunoglobulin according to the invention of known concentrations are used to associate each concentration ($C_n$) of the solutions ($S_n$) of monoclonal chimeric immunoglobulin with a measured value ($V_n$) of a parameter chosen from the group formed of a fluorescence parameter, especially a fluorescence parameter measured by quantitative immunofluorimetry (Luminex® technique using beads coated with HLA antigens) or by the flow cytometry technique (carried out with lymphocytes), a luminescence parameter, especially a chemiluminescence parameter, and a colorimetry parameter.

Advantageously, in a process according to the invention, each monoclonal antibody specific to monomorphic epitopes of HLA class I antigens and each monoclonal antibody specific to monomorphic epitopes of HLA class II antigens is chosen from the group formed of the monoclonal antibodies of a vertebrate, in particular the monoclonal antibodies of a mammal, especially of a mouse, rat, rabbit, hamster and of a human, and the monoclonal antibodies of a non-mammalian vertebrate, especially of an amphibian, of a bird, in particular of a galliforme.

Advantageously and according to the invention, the parameter is chosen from the group formed of fluorescence parameters, luminescence parameters and colorimetry parameters.

Advantageously and according to the invention, the fluorescence parameter is a fluorescence intensity. Accordingly, each value ($V_n$) of the fluorescence parameter is a fluorescence intensity.

Advantageously and according to the invention, each measured value ($V_n$) of the parameter is measured by a technique chosen from the group formed of multiplex quantitative immunofluorimetry, flow cytometry, a method of immunoenzymatic assay on a solid substrate (ELISA), a competitive binding method and a complement-dependent microlymphocytotoxicity method.

Advantageously, in a first variant of a process according to the invention:
a) each immobilised HLA antigen being an HLA antigen immobilised on a solid substrate in the divided state formed of particles,
b) the immobilised HLA antigens and each solution of monoclonal chimeric immunoglobulin directed against the HLA antigens of the solid substrate are brought into contact under conditions suitable for forming a stable bond between the HLA antigens of the solid substrate and the monoclonal chimeric immunoglobulin of each solution of monoclonal chimeric immunoglobulin, and then
c) the monoclonal chimeric immunoglobulins that are not bound to the HLA antigens of the solid substrate are removed by washing, and then
d) the monoclonal chimeric immunoglobulins that are bound to the HLA antigens of the solid substrate are brought into contact with a solution of a secondary antibody which is chosen from the group formed of fluorescent secondary antibodies, luminescent secondary antibodies and photoabsorbent secondary antibodies and which is directed against the monoclonal chimeric immunoglobulin, under conditions suitable for forming a stable bond between the monoclonal chimeric immunoglobulin and the secondary antibody, and then
e) the secondary antibody that is not bound to the monoclonal chimeric immunoglobulin is removed by washing, and then
f) at least one parameter of the secondary antibody that is bound to each particle of the solid substrate is measured, and there is assigned to that measurement a measured value ($V_n$) of said parameter chosen from the group formed of a fluorescence parameter, especially a fluorescence parameter measured by quantitative immunofluorimetry (Luminex® technique using beads coated with HLA antigens) or by the flow cytometry technique (carried out with lymphocytes), a luminescence parameter, especially a chemiluminescence parameter, and a colorimetry parameter, and then
g) the calibration curve is formed, and then
h) there is derived from the calibration curve a fluorescence intensity threshold value indicating the presence of the anti-HLA antibody in a solution to be analysed.

Advantageously, in a second variant and according to the invention, each immobilised HLA antigen is an HLA antigen presented on the surface of at least one cell, especially a cell in in vitro culture.

Advantageously, in this second variant of a process according to the invention:
i) each immobilised HLA antigen being an HLA antigen presented on the surface of at least one cell,
j) the HLA antigens presented on the surface of at least one cell and each solution of monoclonal chimeric immunoglobulin are brought into contact under conditions suitable for forming a stable bond between the HLA antigens of the cell(s) and the monoclonal chimeric immunoglobulin of each solution of monoclonal chimeric immunoglobulin, and then
k) the monoclonal chimeric immunoglobulin that is not bound to the HLA antigens of the cell(s) is removed by washing, and then
l) the monoclonal chimeric immunoglobulin that is bound to the HLA antigens of the cell(s) is brought into contact with a solution of a secondary antibody directed against the monoclonal chimeric immunoglobulin, under conditions suitable for forming a stable bond between the monoclonal chimeric immunoglobulin and the secondary antibody, and then
m) the secondary antibody that is not bound to the monoclonal chimeric immunoglobulin is removed by washing, and then
n) at least one parameter of the secondary antibody that is bound to each cell is measured, and there is assigned to that measurement a measured value ($V_n$) of said parameter chosen from the group formed of a fluorescence parameter, especially a fluorescence parameter measured by quantitative immunofluorimetry (Luminex® technique using beads coated with HLA antigens) or by the flow cytometry technique (carried out with lymphocytes), a luminescence parameter, especially a chemiluminescence parameter, and a colorimetry parameter, and then
o) the calibration curve is formed, and then
p) there is derived from the calibration curve a fluorescence intensity threshold value indicating the presence of the anti-HLA antibody in a solution to be analysed.

Advantageously and according to the invention, the solid substrate in the divided state is in the form of particles of substantially spherical shape and of a size suitable for permitting their analysis by flow fluorimetry.

Advantageously and according to the invention, the calibration curve is determined by non-linear regression from fluorescence intensity measurements.

Advantageously and according to the invention, the liquid medium is chosen from the group formed of biological fluids, especially a serum, collected from an individual.

Advantageously and according to the invention, the individual is a patient chosen from the group formed of patients awaiting a transplant and transplant patients.

Advantageously and according to the invention, the monoclonal antibody specific to monomorphic epitopes of HLA class I antigens is the W6/32 antibody.

Advantageously and according to the invention, the monoclonal antibody specific to monomorphic epitopes of HLA class II antigens is the F.3.3 antibody.

The invention extends in addition to a kit for the quantification of anti-HLA antibodies in a liquid medium, said kit comprising at least one monoclonal chimeric immunoglobulin comprising:

two polypeptide chains, called heavy chains (H), of molecular weight from 40 kDa to 60 kDa, and
two polypeptide chains, called light chains (L), of molecular weight from 20 kDa to 30 kDa,
wherein:
each heavy chain (H) comprises:
  a heavy chain variable region ($V_H$) of a monoclonal antibody chosen from the group formed of monoclonal antibodies specific to monomorphic epitopes of HLA class I antigens and monoclonal antibodies specific to monomorphic epitopes of HLA class II antigens, and
  a heavy chain constant region ($C_H$) of a human immunoglobulin chosen from the group formed of IgAs, IgGs and IgMs,
and in that
each light chain (L) comprises:
  a light chain variable region ($V_L$) of a monoclonal antibody chosen from the group formed of monoclonal antibodies specific to monomorphic epitopes of HLA class I antigens and monoclonal antibodies specific to monomorphic epitopes of HLA class II antigens, and
  a light chain constant region ($C_L$) of a human immunoglobulin chosen from the group formed of the kappa chains and the lambda chains.

The invention relates also to an antibody, a process and a kit, characterised in combination by all or some of the features mentioned hereinabove or herein below.

BRIEF DESCRIPTION OF THE DRAWINGS

Other objects, features and advantages of the invention will become apparent upon reading the following description, which makes reference to the accompanying figures showing preferred embodiments of the invention, given solely by way of non-limiting examples, and in which:

FIG. 4 is a comparative representation in histogram form of the fluorescence intensity of a positive control according to the prior art and a positive control according to the invention, in which:

FIG. 4A is a representation in histogram form of the fluorescence intensity measured on 12 types of HLA class I beads treated with a positive control according to the prior art (hatched histogram) and with a positive control according to the invention (solid histogram);

FIG. 4B is a representation in histogram form of the fluorescence intensity measured on 5 types of HLA class II beads treated with a positive control according to the prior art (hatched histogram) and with a positive control according to the invention (solid histogram);

FIG. 9 is a representation of the peptide sequence of the light chain of the monoclonal chimeric immunoglobulin Hu-IgG1 K [W6/32] (SEQ ID NO: 1);

FIG. 10 is a representation of the peptide sequence of the heavy chain of the monoclonal chimeric immunoglobulin Hu-IgG1 K [W6/32] (SEQ ID NO: 2);

FIG. 11 is a representation of the peptide sequence of the heavy chain of the monoclonal chimeric immunoglobulin Hu-IgA2 K [W6/32] (SEQ ID NO: 3);

FIG. 12 is a representation of the peptide sequence of the heavy chain of the monoclonal chimeric immunoglobulin Hu-IgM K [W6/32] (SEQ ID NO: 4);

FIG. 13 is a representation of the peptide sequence of the light chain of the monoclonal chimeric immunoglobulin Hu-IgG1 K [F3.3] (SEQ ID NO: 5);

FIG. 14 is a representation of the peptide sequence of the heavy chain of the monoclonal chimeric immunoglobulin (IgA2-anti-HLA class II) (SEQ ID NO: 6);

FIG. 15 is a representation of the peptide sequence of the heavy chain of the monoclonal chimeric immunoglobulin (IgG1-anti-HLA class II) (SEQ ID NO: 7);

FIG. 16 is a representation of the peptide sequence of the heavy chain of the monoclonal chimeric immunoglobulin (IgM-anti-HLA class II) (SEQ ID NO: 8).

DETAILED DESCRIPTION OF THE INVENTION

Example 1

Figure 1:
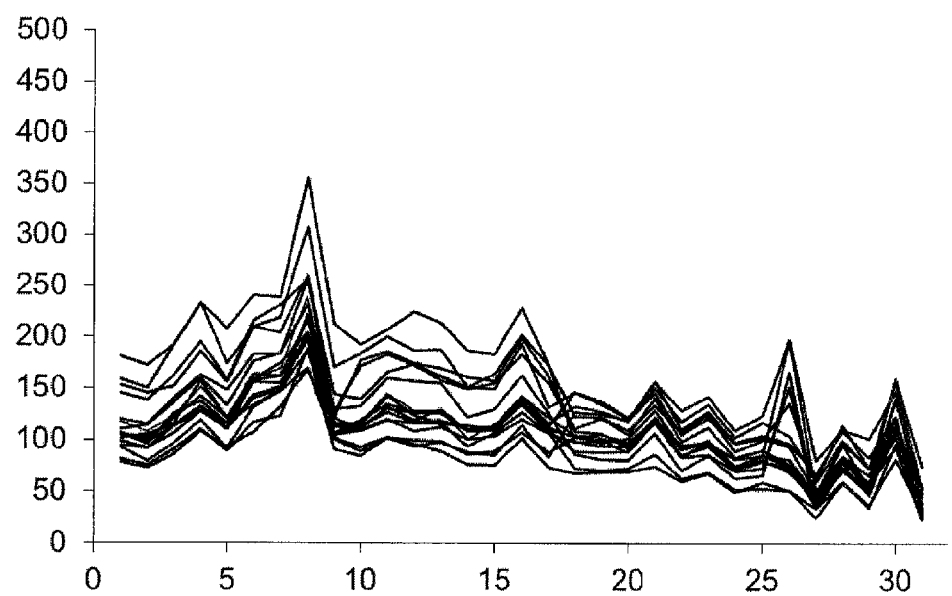
FIG. 1 is a graphical representation of the variation over time of the fluorescence intensity of 17 types of beads treated according to a negative control.
Figure 2:
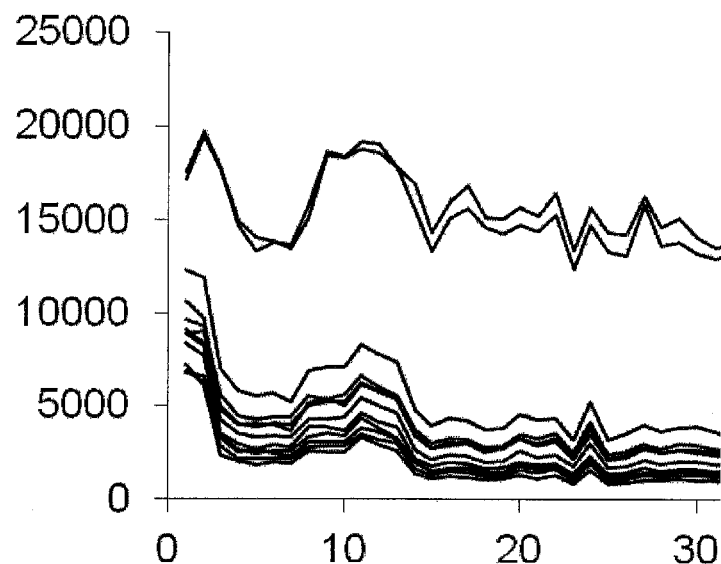
FIG. 2 is a graphical representation of the variation of the fluorescence intensity of 12 types of beads carrying HLA class I antigens of a positive control according to the prior art as a function of time.
Figure 3:
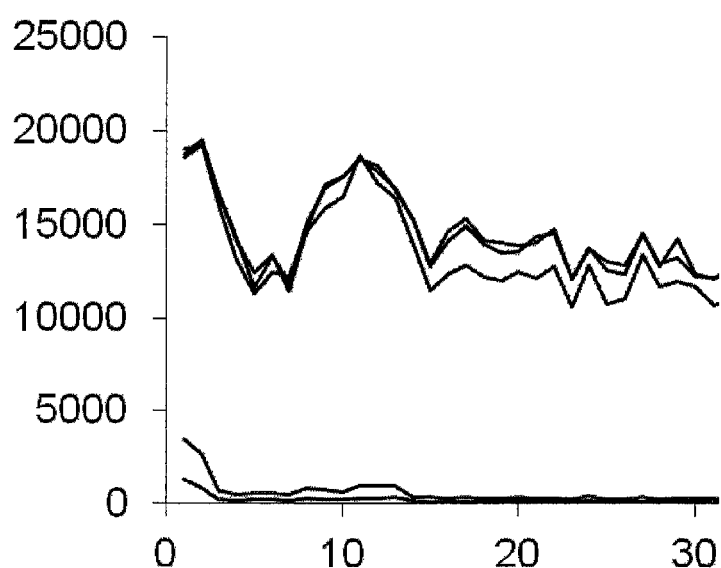
FIG. 3 is a graphical representation of the variation of the fluorescence intensity of 5 types of HLA class II beads of a positive control according to the prior art as a function of time.

Production of a IgG/Anti-HLA Class I Monoclonal Chimeric Immunoglobulin (Hu-IgG1 K [W6/32]) According to the Invention The W6/32 antibody was described for the first time in the publication of Barnstable et al. in 1978 (Barnstable C J, Bodmer W F, Brown G, Galfre G, Milstein C, Williams A F, Ziegler A., 1978, Celle, 14(1), 9-20. *Production of monoclonal antibodies to group A erythrocytes, HLA and other human cell surface antigens-new tools for genetic analysis*). This antibody is secreted by a mouse hybridoma coming from the fusion of cells of a mouse myeloma line (P3-NSI/1Ag4-1 line which does not secrete mouse immunoglobulin) with the lymphocytes of a mouse immunised against human cells. It has been shown that this antibody reacts with a public epitope found on the HLA class I molecules (HLA-A, HLA-B, HLA-C). The recognised epitope is a conformational epitope which depends on the association between the class I alpha heavy chain and beta-2 microglobulin. The epitope requires the presence of an arginine at position 3 of the beta-2 microglobulin and a lysine at position 121 of the alpha chain (Ladasky J J, Shum B P, Canavez F, Seuánez H N, Parham P., (1999), Immunogenetics, 49(4), 312-320. *Residue 3 of beta2-microglobulin affects binding of class I MHC molecules by the W6/32 antibody*).

In a first step, the transcripts coding for the heavy chain and the light chain of the W6/32 antibody were cloned and sequenced.

The DNA copy of the mRNAs (cDNAs) of the heavy chain was amplified by PCR with the aid of two primers, one specific to the region coding for the leader peptide, the other targeting the 5' part which codes for the CH1 domain of the constant part.

For the amplification of the cDNA of the light chain, a primer targeting the exon of the leader peptide and a primer targeting the 5' part of the C kappa domain were used. The cDNA fragments of the two chains were cloned in *E. coli*. The cloned fragments were sequenced. Alignment of the sequences allowed the consensus of the cDNAs of the heavy chain and of the light chain to be established with an identity threshold of 98%. The regions coding for the variable parts were determined by comparison with the sequences present in the IMGT® ("International Immunogenetics Information System") data bank.

Sequences coding for a light chain or heavy chain leader peptide, as appropriate, were added at 5', and the sequences at 3' were modified so as to create a BsiWI restriction site for the DNA of the light chain and a NheI restriction site for the heavy chain. These restriction sites are suitable for permitting an insertion of these nucleic sequences into the cloning vectors pFUSE-CLig and pFUSE-CHIg (InvivoGen, Toulouse, France). The sequences so defined were synthesised and then cloned in expression vectors comprising either the part coding for the constant domain of the human kappa chain (allotype Km 01; Genbank accession number: J00241) or the constant part of the human IgG1s (allotype G1m17,1; Genbank accession number: J00228). The restriction site of the expression vector permits insertion of the cDNAs of the variable parts in phase with the regions coding for the constant parts of the immunoglobulin chains.

Two expression vectors, one coding for a chimeric light chain associating the variable part of the light chain of the W6/32 antibody and the human C kappa domain (VL [W6/32]-human C kappa chain), the other associating the variable part of the heavy chain of the W6/32 antibody and the human C gamma 1 domain were thus obtained.

These two vectors were introduced by transfection into CHO cells (Chinese Hamster Ovary cells). To that end, the cells were first transfected by the vector coding for the light chain and then by the vector coding for the heavy chain. The expression vectors comprise cytotoxic drug resistance factors which allow the double-transfected cells to be selected effectively. After the selection period, the double-transfected cells were cloned by limiting dilution and the presence of the human IgG1 kappa was revealed in the supernatant of the clones by a sandwich ELISA technique. The producer clones so revealed were subjected to a plurality of cloning cycles by limiting dilution in such a manner as to recruit the most effective clones in the secretion of the chimeric IgG1 kappa, denoted Hu-IgG1 K [W6/32] hereinbelow.

The Hu-IgG1 K [W6/32] secreted in the culture supernatant of the transfected CHO cells were purified by capture elution on staphylococcal protein A bound to Sepharose® beads. The IgG1 kappa were eluted at acid pH in a glycine buffer at pH 2. The eluate was buffered extemporaneously with an aqueous solution of disodium phosphate at a concentration of 750 mM. The solutions of Hu-IgG1 K [W6/32] are stored at 4° C. or at −80° C.

The peptide sequence of the light chain of the monoclonal chimeric immunoglobulin (IgG1 anti-HLA class I) Hu-IgG1 K [W6/32] is shown in FIG. 9. The peptide sequence of the heavy chain of the monoclonal chimeric immunoglobulin (IgG1 anti-HLA class I) Hu-IgG1 K [W6/32] is shown in FIG. 10.

Verification of the specificity of the binding of the monoclonal chimeric immunoglobulin Hu-IgG1 K [W6/32] according to the invention was carried out on T lymphocytes or on B lymphocytes separated on a density gradient, starting from human blood collected using an EDTA tube. The cells were labelled with anti-CD3, anti-CD19 and anti-CD45 antibodies. The T lymphocytes (CD3+) and B lymphocytes (CD19+) are defined among the population of the CD45+ lymphocytes.

Figure 5:
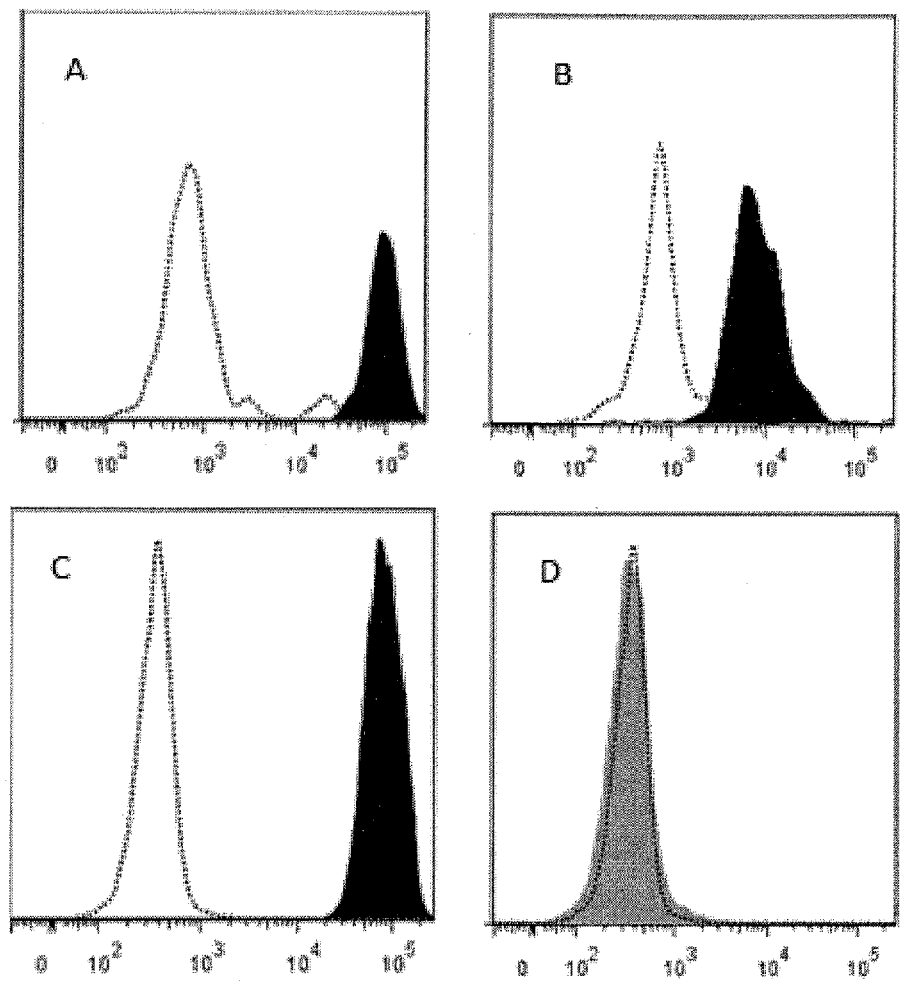
FIG. 5 is an analysis by flow cytometry of the fixing of class I and class II chimeric monoclonal immunoglobulins according to the invention to T lymphocytes and B lymphocytes.

The monoclonal chimeric immunoglobulin Hu-IgG1 K [W6/32] is incubated in the presence of human mononuclear cells (T lymphocytes or B lymphocytes) of the peripheral blood, and then said human mononuclear cells are washed three times in succession followed by washing three times in phosphate buffered saline (PBS). The fixing of the monoclonal chimeric immunoglobulins fixed to the human mononuclear cells is revealed by means of goat anti-human Fcγ antibodies. The results are presented in FIG. 5 and show that the Hu-IgG1 K [W6/32] antibody fixes itself to the B lymphocytes (FIG. 5A) and to the T lymphocytes (FIG. 5C), whereas the Hu-IgG1 K [F3.3] antibody fixes itself to the B lymphocytes (FIG. 5B) and not to the T lymphocytes (FIG. 5D).

Example 2

Specificity of the Monoclonal Chimeric Immunoglobulins Hu-IgG1 K [W6/32]

The specificity of the monoclonal chimeric immunoglobulins Hu-IgG1 K [W6/32] was then determined by a technique of multiplex quantitative fluorimetry using commercial kits distributed by the company One Lambda®. This determination is based on an indirect immunofluorescence reaction and uses latex beads coated with HLA antigen of different groups. The antibodies capable of recognising the HLA antigens present on the latex beads are revealed by anti-human IgG antibodies coupled to phycoerythrin. The fluorescence is quantified on each bead by flow cytometry in a Luminex® apparatus. Specific fluorescent labelling of each type of beads allows several varieties of beads (recognisable by their fluorescence) to be used, each bead being coated with a given mixture of HLA antigens. This makes it possible to show that all the class I beads are recognised with substantially the same intensity (FIG. 4A, class I beads). This allows us to conclude that the monoclonal chimeric immunoglobulin Hu-IgG1 K [W6/32] recognises a public epitope present on all the HLA class I molecules.

Competition experiments have made it possible to show that the W6/32 mouse monoclonal antibody secreted by the mouse hybridoma inhibits the fixing of the monoclonal chimeric immunoglobulin Hu-IgG1 K [W6/32].

Example 3

Production of Anti-HLA Class I Chimeric Monoclonal Antibodies of Isotype IgA2 and IgM (Hu-IgA2 K [W6/32] and Hu-IgM K [W6/32]) According to the Invention The W6/32 heavy chain variable part (VH[W6/32]) was cloned in two other expression vectors; the first permits the production of chimeric mu chains (variable part of W6/32 and constant part of the human mu heavy chain (Genbank accession number: AY510104.1), the other permits the production of chimeric alpha 2 chains (variable part of W6/32 and constant part of the human alpha 2 heavy chain, allotype A2m(1) (Genbank accession number: J00221). These two vectors were used to transfect cells of the line CHO previously transfected by the vector permitting expression of the human chimeric light chain VL[W6/32]-K. We thus isolated a clone of CHO cells secreting large quantities of monoclonal chimeric immunoglobulin Hu-IgA2 K [W6/32] and another clone secreting a monoclonal chimeric immunoglobulin Hu-IgM K [W6/32]. The chimeric IgAs were purified on an agarose substrate coupled to peptide M (InvivoGen, Toulouse, France) and the chimeric IgMs were purified on an agarose substrate coupled to protein L (InvivoGen, Toulouse, France) according to the supplier's recommendations.

The peptide sequence of the heavy chain of the monoclonal chimeric immunoglobulin (IgA2 anti-HLA class I) Hu-IgA2 K [W6/32] is shown in FIG. 11.

The peptide sequence of the heavy chain of the monoclonal chimeric immunoglobulin (IgM anti-HLA class 1) is shown in FIG. 12.

The reactivity of the monoclonal chimeric immunoglobulins Hu-IgA2 K [W6/32] and Hu-IgM K [W6/32] was verified by the Luminex® technique with Labscreen Mixed® kits (One Lambda®) and, as fluorescent secondary antibodies, goat anti-human IgA or anti-human IgM antibodies coupled to phycoerythrin.

Example 4

Production of an Anti-HLA Class II Monoclonal Antibody (Hu-IgG1 K [F3.3]) According to the Invention In terms of its principle, the process for producing an anti-HLA class II monoclonal antibody is comparable to the process for producing an anti-HLA class I monoclonal antibody (W6/32).

The F3.3 antibody (Elsasser, D., Valerius, T., Repp, R., Weiner, G. J., Deo, Y., Kalden, J. R., van de Winkel, J. G., Stevenson, G. T., Glennie, M. J. and Gramatzki, M., (1996), Blood, 87(9), 3803-3812. *HLA class II as potential target antigen on malignant B cells for therapy with bispecific antibodies in combination with granulocyte colony-stimulating factor*) is the product of a single mouse hybridoma clone. The F3.3 antibody recognises at least one public epitope present on the surface of all human cells that express the HLA class II molecules. In particular, the F3.3 antibody recognises all the DR antigens, all the DP antigens and all the antigens of group DQ2. The complete sequences coding for the variable parts of the F3.3 antibody are accessible on GenBank® (accession numbers: AY058910 [VL] for the light chain and AY058911 [VH] for the heavy chain).

The sequences of the variable parts were synthesised and cloned in phase in the cloning vectors pFUSE-CHIg (InvivoGen, Toulouse, France) for the heavy chains and pFUSE-CLIg (InvivoGen, Toulouse, France) for the light chains. The vector (pFUSE-CHIg) permits the production of the chimeric heavy chain VH[F3.3]-human C gamma 1 and the vector (pFUSE-CLIg) permits the production of the light chain VL[F3.3]-human C kappa. These two expression vectors are used to transfect cells of the line CHO as described in Example 1.

In addition, the variable part VH[F3.3] was cloned in expression vectors permitting the production of chimeric heavy chains VH[F3.3]-human C mu and VH[F3.3]-human C alpha 2.

The peptide sequence of the light chain of the monoclonal chimeric immunoglobulin (IgG1 anti-HLA class II) is shown in FIG. 13.

The peptide sequence of the heavy chain of the monoclonal chimeric immunoglobulin (IgA2 anti-HLA class II) is shown in FIG. 14.

The peptide sequence of the heavy chain of the monoclonal chimeric immunoglobulin (IgG1 anti-HLA class II) is shown in FIG. 15.

The peptide sequence of the heavy chain of the monoclonal chimeric immunoglobulin (IgM anti-HLA class II) is shown in FIG. 16.

The monoclonal chimeric immunoglobulins Hu-IgG1 K [F3.3], Hu-IgA2 K [F3.3] and Hu-IgM K [F3.3] directed against the HLA class II antigens were produced by CHO cells transfected by the appropriate vectors. The chimeric IgG1 were purified on protein A Sepharose. The chimeric IgAs were purified on peptide M-agarose (InvivoGen, Toulouse, France). The chimeric IgMs were purified on protein L-agarose (InvivoGen, Toulouse, France).

The specificity of the binding of the monoclonal chimeric immunoglobulin Hu-IgG1 K [F3.3] according to the invention is verified by a technique of indirect immunofluorescence by flow cytometry on mononuclear human cells as described in Example 1. The results are presented in FIG. 5 and show that the antibody Hu-IgG1 K [F3.3] according to the invention reacts strongly against the human cells, especially with the B lymphocytes (FIG. 5B) and with the T lymphocytes (FIG. 5D).

In addition, the specificity of the anti-HLA class II monoclonal chimeric immunoglobulins according to the invention is studied by the technique of multiplex quantitative immunofluorimetry on Luminex® with the aid of Labscreen Mixed® and Labscreen single Antigen® kits (One Lambda®).

The antibody Hu-IgG1 K [F3.3] fixed itself to all the beads carrying the HLA class II antigens of the Labscreen Mixed® kit and to all the beads carrying the HLA-DR, HLA-DP and HLA-DQ2 antigens of the Labscreen single antigen class II® kit.

It has been shown, by competition experiments, that the monoclonal chimeric immunoglobulins Hu-IgG1 K [F3.3] and Hu-IgA2 K [F3.3] recognise the same epitope. The reactivity of the monoclonal chimeric immunoglobulin Hu-IgA2 K [F3.3] was studied by the Luminex® technique with the Labscreen Mixed® kits (One-Lambda®) using goat anti-human IgA antibodies coupled to phycoerythrin to reveal the fixing of the monoclonal chimeric immunoglobulins Hu-IgA2 K [F3.3]. The reactivity of the monoclonal chimeric immunoglobulin Hu-IgA2 K [F3.3] is found to be identical with that of the monoclonal chimeric immunoglobulin Hu-IgG1 K [F3.3].

Example 5

Process for the In Vitro Quantification of Anti-HLA Antibodies

In a process for the in vitro quantification of anti-HLA antibodies in a liquid medium containing antibodies by immunofluorescence according to the invention, there is used, by way of non-limiting example, a "Labscreen Mixed®" laboratory kit (LSM12, One Lambda® Inc., USA) comprising:
- polystyrene beads covalently bonded to purified HLA class I antigens (HLA-A, HLA-B and HLA-C), and, in admixture,
- polystyrene beads covalently bonded to purified HLA class II antigens (HLA-DR, HLA-DQ and HLA-DP),
- polystyrene beads, called positive control beads, bonded to IgGs,
- polystyrene beads, called negative control beads, without a surface antigen. Such a laboratory kit (Labscreen Mixed®) comprises an aqueous suspension of polystyrene beads for screening anti-HLA class I antibodies and anti-HLA class II antibodies. The polystyrene beads in this suspension comprise a plurality of types of polystyrene beads, each type of polystyrene bead being distinguished from the other types of polystyrene bead by means of a fluorescent marker and comprising polystyrene beads carrying separate HLA class I antigens and HLA class II antigens. In practice, each type of polystyrene bead has on the surface of the polystyrene beads up to six HLA-A (class I) antigens, six HLA-B (class I) antigens, six HLA-C (class I) antigens, or six HLA-DQ (class II) antigens, six HLA-DR (class II) antigens, six HLA-DP (class II) antigens.

The laboratory kit (Labscreen Mixed®) comprises 12 types of class I polystyrene beads and 5 types of class II polystyrene beads, the fluorescence intensity of each of the 17 types of polystyrene beads being able to be measured simultaneously. Accordingly, the average of the fluorescence intensity of each of the types of polystyrene beads bonded to the same group of HLA antigens is calculated. Within the mixture of polystyrene beads, some are without an HLA class I antigen or HLA class II antigen and serve as negative control.

The use of the laboratory kit (Labscreen Mixed®) additionally requires a negative control serum (LabScreen Negative Control (LSNC) serum) in the anti-HLA antibody screening reaction. The serum is characterised by the manufacturer as being without anti-HLA class I antibodies and anti-HLA class II antibodies.

The average values of the fluorescence intensity, observed over a period of five months, associated with each of the 12 types of beads carrying class I antigens and with each of the 5 types of beads carrying class II antigens treated with such a negative control are given in Table 1 below.

TABLE 1

| Class of HLA Ag recognised | Bead number | Average fluorescence | Standard deviation |
| --- | --- | --- | --- |
| Class I | 6 | 79.82 | 30.26 |
| | 7 | 110.87 | 39.45 |
| | 88 | 118.09 | 30.31 |
| | 17 | 94.16 | 38.98 |
| | 69 | 136.93 | 54.01 |
| | 79 | 136.67 | 49.73 |
| | 84 | 109.79 | 35.61 |
| | 86 | 102.07 | 27.77 |
| | 87 | 119.96 | 32.50 |
| | 88 | 100.67 | 30.04 |
| | 89 | 90.89 | 25.85 |
| | 90 | 157.12 | 73.60 |
| Class II | 91 | 112.79 | 35.91 |
| | 93 | 143.52 | 39.21 |
| | 95 | 104.89 | 34.79 |
| | 96 | 153.14 | 55.02 |
| | 97 | 117.61 | 46.14 |

The values presented in Table 1 are low and reflect the fluorescence generated by the non-specific binding of the IgGs to the polystyrene beads, and the non-specific binding of the secondary antibody to the beads.

Positive Control

The laboratory kit (Labscreen Mixed®) comprises, as positive control, polystyrene beads to the surface of which there are grafted purified human IgGs. Such a positive control is limited in its use to the verification of the functionality of the secondary antibody. Such a positive control does not allow a value of the fluorescence intensity to be converted into a value of the concentration of anti-HLA antibodies in a liquid medium.

Polyclonal Positive Control

The users of the kit (Labscreen Mixed®), especially immunology laboratories, recommend using, as positive control in the screening of anti-HLA antibodies in vitro according to the prior art, a mixture of serums collected from individuals polyimmunised against the HLA antigens. By way of example, the average values of the fluorescence intensity, measured over a period of 5 months, associated with each type of HLA class I and class II beads of this polyclonal control are given in Table 2 below.

TABLE 2

| Class of HLA Ag recognised | Bead number | Average fluorescence | Standard deviation |
| --- | --- | --- | --- |
| Class I | 6 | 3821.21 | 1980.68 |
| | 7 | 5313.44 | 2261.91 |
| | 88 | 4103.80 | 1812.89 |
| | 17 | 3808.23 | 1726.83 |
| | 69 | 2699.31 | 1759.92 |
| | 79 | 2316.98 | 1341.26 |
| | 84 | 2437.50 | 1672.73 |
| | 86 | 3163.40 | 1765.90 |
| | 87 | 1836.57 | 1379.55 |
| | 88 | 2082.32 | 1364.82 |
| | 89 | 15691.55 | 1791.89 |
| | 90 | 15158.40 | 2072.65 |

TABLE 2-continued

| Class of HLA Ag recognised | Bead number | Average fluorescence | Standard deviation |
|---|---|---|---|
| Class II | 91 | 14433.92 | 2197.01 |
| | 93 | 13343.17 | 2492.20 |
| | 95 | 14550.62 | 2162.28 |
| | 96 | 207.17 | 232.44 |
| | 97 | 589.34 | 670.31 |

The calculated value of the average fluorescence measured on the HLA class I beads treated with a qualitative control according to the prior art is approximately 5200 fluorescence units, and the standard deviation is approximately 4900 fluorescence units.

The calculated value of the average fluorescence measured on the HLA class II beads treated with a qualitative control according to the prior art is approximately 8600 fluorescence units, and the standard deviation is approximately 7500 fluorescence units.

The fluorescence intensity of each of the types of polystyrene bead of the qualitative control varies between 1000 and 20,000. Such variability in the response of each of the types of polystyrene beads (HLA-A, HLA-B, HLA-C, HLA-DQ, HLA-DR and HLA-DP) does not allow a single curve for conversion of the measured fluorescence intensity into a reference anti-HLA antibody concentration to be defined. In addition, such a curve for conversion of the measured fluorescence intensity cannot be obtained, given the fact that the concentration of HLA antibodies specific to each of the types of HLA antigen cannot be determined in the qualitative control of the prior art.

By way of example of a qualitative control of the prior art, an analysis of the fluorescence of each type of polystyrene bead of the "Labscreen Mixed®" kit shows that the fluorescence associated with each type of bead carrying a class I antigen (bead type no. 6, 7, 8, 17, 69, 79, 84, 86, 87, 88, 89 and 90 in FIG. 4A) varies between a value of approximately 7000 average fluorescence units and 12,000 average fluorescence units. The average value of the fluorescence intensities measured on each type of HLA class I bead is approximately 9600 fluorescence units. The value of the standard deviation of these values is approximately 3100 fluorescence units.

In addition, this analysis of the fluorescence of each type of polystyrene bead of the "Labscreen Mixed®" kit shows that the fluorescence associated with each type of bead carrying a class II antigen (bead type no. 91, 93, 95, 96 and 97 in FIG. 4B) varies between a value of approximately 1000 average fluorescence units and 19,000 average fluorescence units. The average value of the fluorescence intensities measured on each type of HLA class II bead is approximately 13,000 fluorescence units. The value of the standard deviation of these values is approximately 8300 fluorescence units.

Such a control is therefore limited in its use to a purely qualitative analysis since the concentration of each antibody in the serum mixture is not known.

Monoclonal Chimeric Immunoglobulin According to the Invention

There is used, as quantitative control of the laboratory kit (Labscreen Mixed®), a monoclonal chimeric immunoglobulin according to the invention. Solutions of an anti-HLA class I monoclonal chimeric immunoglobulin (Hu-IgG1 K [W6/32]) and/or of an anti-HLA class II monoclonal chimeric immunoglobulin (Hu-IgG1 K [F3.3]) as described in Examples 1 to 4 at a known concentration of 2 µg/ml are prepared. An analysis of the average fluorescence intensity associated with each type of polystyrene bead carrying an HLA class I or class II antigen is carried out. The results obtained are presented in FIG. 4 (white histograms).

For each type of polystyrene bead of the "Labscreen Mixed®" kit, a fluorescence intensity of approximately 22,000 average fluorescence units is observed.

In particular, this analysis shows that:
the fluorescence associated with each type of bead carrying a class I antigen (bead type no. 6, 7, 8, 17, 69, 79, 84, 86, 87, 88, 89 and 90 in FIG. 4A, solid histograms) is substantially constant and is approximately 22,000 average fluorescence units. The average value of the fluorescence intensities measured on each type of HLA class I bead is approximately 21,500 fluorescence units. The value of the standard deviation of these values is approximately 450 fluorescence units;
the fluorescence associated with each type of bead carrying a class II antigen (bead type no. 91, 93, 95, 96 and 97 in FIG. 4B, solid histograms) is substantially constant and is approximately 22,000 average fluorescence units. The value of the standard deviation of these values is approximately 700 fluorescence units.

This fluorescence intensity value is substantially constant whatever the type of polystyrene bead (whatever the HLA antigen carried by the type of polystyrene bead) and corresponds to an antibody concentration of 2 µg/ml. Such chimeric monoclonal antibodies according to the invention are suitable for permitting a quantitative calibration of the fluorescence response as a function of the concentration of chimeric monoclonal antibodies according to the invention.

Figure 4:
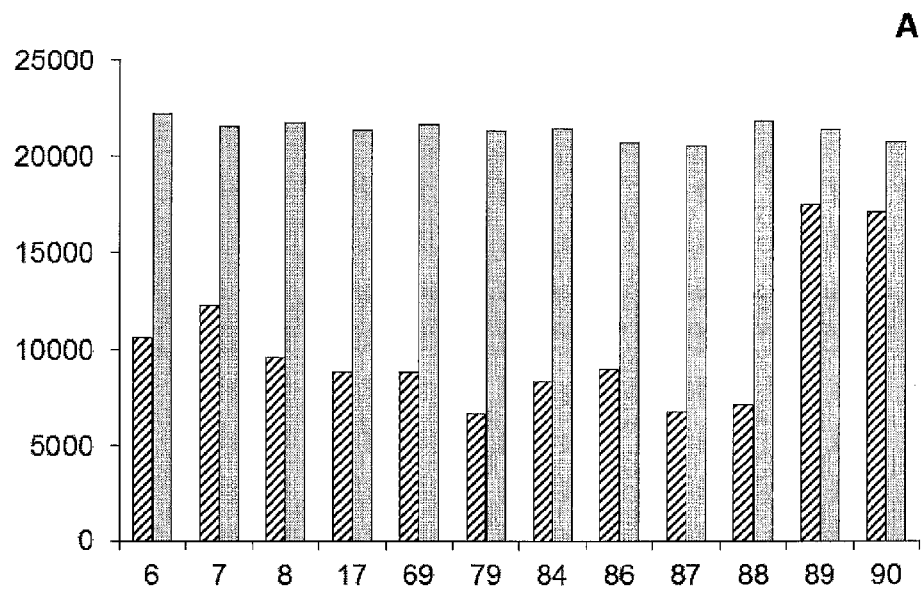
Figure 4:
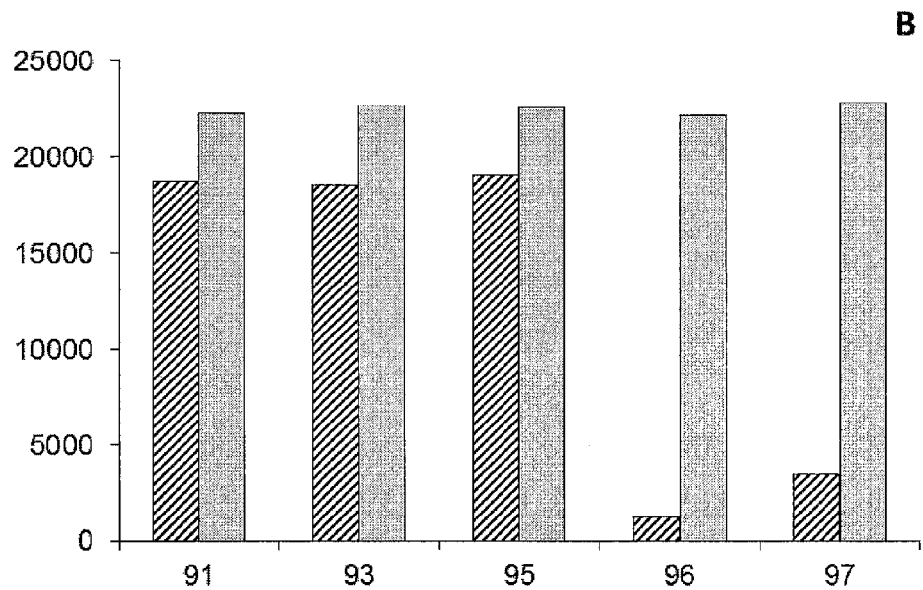

By way of comparison of the invention (solid histograms in FIGS. 4A and 4B) and of the prior art (hatched histograms in FIGS. 4A and 4B), the average fluorescence values (and standard deviation) found on the beads carrying HLA class I antigens and on the beads carrying HLA class II antigens are shown in FIG. 4.

Example 6

Process for the In Vitro Quantification of Anti-HLA Antibodies—"Dose/Response" Curves In order to produce a "dose/response" curve, 300 µl of a washing buffer (PBS) are distributed in each of the wells of a multi-well microfilter plate (Multiscreen®). After 10 minutes, the washing buffer is removed by suction, and 5 µl of homogenised bead suspension "Labscreen Mixed®" are added. A range of solutions of chimeric monoclonal antibodies according to the invention of decreasing concentrations of chimeric monoclonal antibodies is obtained by successive serial dilutions. The negative and positive controls are treated in the same way in parallel. 20 µl of each of the serial dilutions are placed in contact with polystyrene beads which have previously been placed in the wells of the multi-well plate. The mixtures of polystyrene beads and chimeric monoclonal antibodies are incubated at ambient temperature and with the exclusion of light for 30 minutes. At the end of the incubation, each of the wells is washed five times in succession with 250 µl of a washing buffer. 100 µl of a solution of secondary antibody diluted to ¹/₁₀₀ are then added. The secondary antibodies used for the fluorescent labelling of the anti-HLA antibodies bound to the polystyrene beads are, for example, goat anti-IgA antibodies coupled to phycoerythrin (anti-IgA-PE, AbSerotec, USA) or goat anti-IgG antibodies coupled to phycoerythrin (anti- IgG-PE, InGen, USA). Of course, any other fluorescent group coupled to an antibody capable of recognising and binding to the constant chains of the monoclonal chimeric immunoglobulin according to the invention may be used. The multi-well plates are placed away from the light and at ambient temperature for 30 minutes, before being analysed in a Luminex® immunofluorescence reader.

Figure 6:
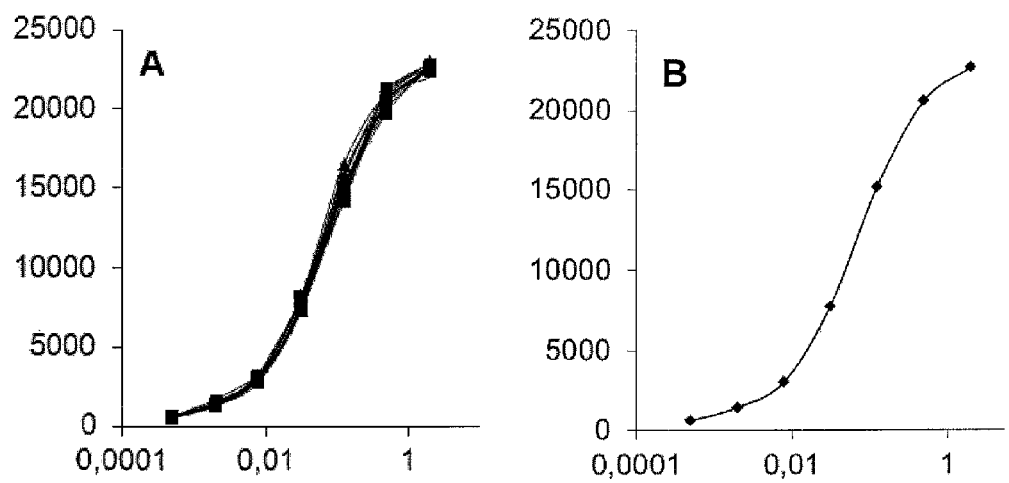
FIG. 6A is a graphical representation of 12 superposed dose/response curves corresponding to 12 types of HLA class I beads treated with a positive control according to the invention. The concentration of monoclonal chimeric immunoglobulin according to the invention is expressed in µg/ml.
FIG. 6B is a graphical representation of the average dose/response curve of 12 types of HLA class I beads treated with a positive control according to the invention corresponding to FIG. 6A. The concentration of monoclonal chimeric immunoglobulin according to the invention is expressed in µg/ml.

Calibration curves of the "dose/response" type obtained by a process according to the invention are shown in FIGS. 6 (anti-HLA class I) and 7 (anti-HLA class II). The value of the fluorescence intensity is given as a function of the concentration of monoclonal chimeric immunoglobulin according to the invention expressed in µg/ml.

Figure 7:
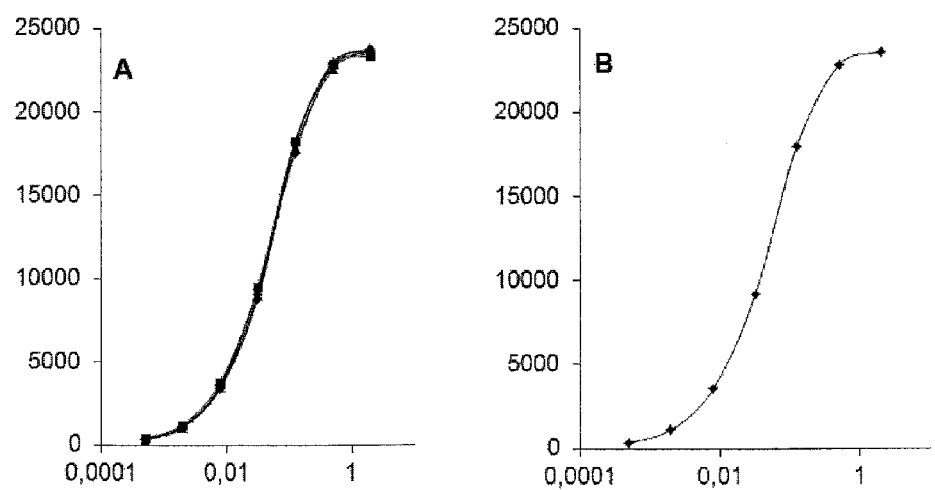
FIG. 7A is a graphical representation of 5 superposed dose/response curves corresponding to 5 types of HLA class II beads treated with a positive control according to the invention. The concentration of monoclonal chimeric immunoglobulin according to the invention is expressed in µg/ml.
FIG. 7B is a graphical representation of the average dose/response curve of the 5 types of HLA class II beads treated with a positive control according to the invention corresponding to FIG. 7A. The concentration of monoclonal chimeric immunoglobulin according to the invention is expressed in µg/ml.

The average values and the standard deviations of the fluorescence intensity measurement measured on each type of HLA class I beads (FIG. 6B) and HLA class II beads (FIG. 7B) are summarised in Table 3 below.

TABLE 3

| Antibody, µg/ml | HLA class I | | HLA class II | |
|---|---|---|---|---|
| | Average | Standard deviation | Average | Standard deviation |
| $5 \times 10^{-4}$ | 589.25 | 31.15 | 316.30 | 29.6 |
| $2 \times 10^{-3}$ | 1433.18 | 103.03 | 1086.38 | 72.15 |
| $7.8 \times 10^{-3}$ | 3028.43 | 143.22 | 3518.68 | 145.09 |
| $3.13 \times 10^{-2}$ | 7781.63 | 342.02 | 9129.82 | 273.56 |
| $1.25 \times 10^{-1}$ | 15190.29 | 685.49 | 17955.55 | 298.79 |
| $5 \times 10^{-1}$ | 20548.53 | 441.7 | 22755.75 | 160.45 |
| $2 \times 10^{0}$ | 22621.17 | 255.88 | 23578.19 | 167 |

A statistical analysis by sigmoid non-linear regression of the Boltzmann type is carried out on the data relating to the titration curves described above. There are determined the minimum observed fluorescence value (MIN), that is to say the value of the asymptote of the curve when the concentration of monoclonal chimeric immunoglobulin tends towards the value 0, the maximum observed fluorescence value (MAX), that is to say the value of the asymptote of the curve when the concentration of monoclonal chimeric immunoglobulin tends towards the infinite value, and the value of the concentration of monoclonal chimeric immunoglobulin corresponding to 50% of the specific signal (MAX-MIN). These values are given in Table 4 below.

TABLE 4

| Monoclonal chimeric immunoglobulin | MIN | MAX | (MAX-MIN)*50%, µg/ml |
|---|---|---|---|
| Anti-class I | 65 | 22400 | 0.06 |
| Anti-class II | 88 | 24600 | 0.05 |

Example 7

Figure 8:
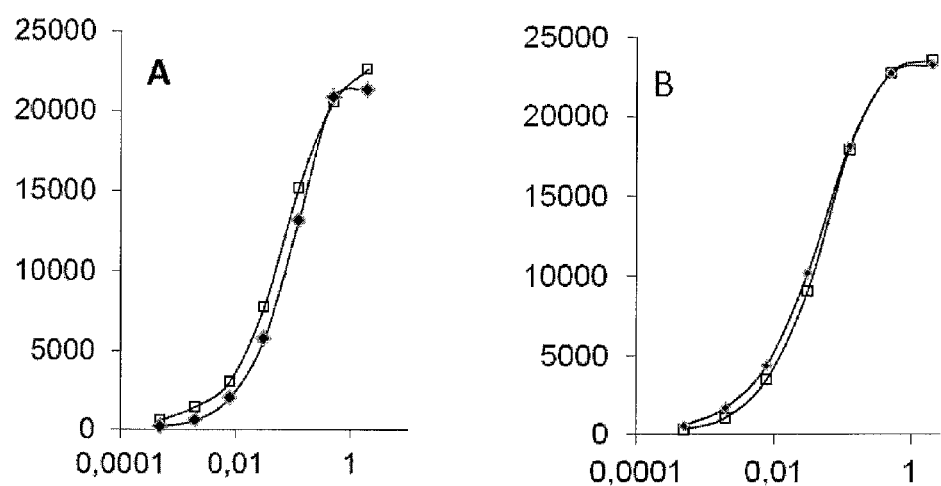
FIG. 8A is a comparative graphical representation of the dose/response curve of an anti-HLA class I monoclonal chimeric immunoglobulin according to the invention stored in a saline buffer (white square) and stored in a solution of human albumin at 60 g/l (black lozenge)
FIG. 8B is a comparative graphical representation of the dose/response curve of an anti-HLA class II monoclonal chimeric immunoglobulin according to the invention stored in a saline buffer (white square) and stored in a solution of human albumin at 60 g/l (black lozenge)

Analysis of the Stability of the Monoclonal Chimeric Immunoglobulins Hu-IgG1 K [W6/32] and Hu-IgG1 K [F3.3] According to the Invention in an Albuminous Buffer Medium Serial dilutions of the monoclonal chimeric immunoglobulins according to the invention stored for a period of two months in an aqueous buffer medium containing human albumin at a concentration of 60 g/l are prepared. "Dose/response" curves as described in Example 6 are prepared by the Luminex® technique. The results obtained with the monoclonal chimeric immunoglobulin directed against the HLA class I antigens (Hu-IgG1 K [W6/32]) are presented in FIG. 8A and the results obtained with the monoclonal chimeric immunoglobulin directed against the HLA class II antigens (Hu-IgG1 K [F3.3]) are presented in FIG. 8B. The results obtained with the monoclonal chimeric immunoglobulins stored in the saline buffer are identified by white squares (□) and the results obtained with the monoclonal chimeric immunoglobulins stored in the albuminous buffer are identified by black lozenges (♦). No significant difference is observed between the monoclonal chimeric immunoglobulins stored in saline buffer and the monoclonal chimeric immunoglobulins stored in albuminous buffer.

The invention claimed is:

1. A monoclonal chimeric comprising formed of:
   (i) two polypeptide chains, called heavy chains (H), of molecular weight from 40 kDa to 60 kDa, and
   (ii) two polypeptide chains, called light chains (L), of molecular weight from 20 kDa to 30 kDa,
   wherein
   each heavy chain (H) comprises:
   a heavy chain variable region (VH) of a monoclonal antibody chosen from the group consisting of monoclonal antibodies specific to monomorphic epitopes of HLA class II antigens, and
   a heavy chain constant region (CH) of a human immunoglobulin chosen from the group consisting of IgAs, IgGs and IgMs,
   and wherein
   at least one light chain (L) consists of the sequence SEQ ID NO: 5, and
   at least one heavy chain (H) is selected from the group consisting of SEQ ID NO: 6, SEQ ID NO: 7 and SEQ ID NO: 8.

2. The monoclonal antibody according to claim 1, wherein the at least one heavy chain (H) consists of the sequence of SEQ ID NO: 6.

3. The monoclonal antibody according to claim 1, wherein the at least one heavy chain (H) consists of the sequence of SEQ ID NO: 7.

4. The monoclonal antibody according to claim 1, wherein the at least one heavy chain (H) consists of the sequence of SEQ ID NO: 8.

5. A kit for the quantification of anti-HLA antibodies in a liquid medium, said kit comprising the monoclonal chimeric immunoglobulin of claim 1.

* * * * *

UNITED STATES PATENT AND TRADEMARK OFFICE
CERTIFICATE OF CORRECTION

PATENT NO. : 9,637,538 B2
APPLICATION NO. : 13/869477
DATED : May 2, 2017
INVENTOR(S) : Antoine Blancher et al.

It is certified that error appears in the above-identified patent and that said Letters Patent is hereby corrected as shown below:

In the Claims

In Column 27, Claim 1, delete:
"1. A monoclonal chimeric comprising formed of:
(i) two polypeptide chains, called heavy chains (H), of molecular weight from 40 kDa to 60 kDa, and
(ii) two polypeptide chains, called light chains (L), of molecular weight from 20 kDa to 30 kDa,
wherein each heavy chain (H) comprises:
a heavy chain variable region (VH) of a monoclonal antibody chosen from the group consisting of monoclonal antibodies specific to monomorphic epitopes of HLA class II antigens, and
a heavy chain constant region (CH) of a human immunoglobulin chosen from the group consisting of IgAs, IgGs and IgMs,
and wherein
at least one light chain (L) consists of the sequence SEQ ID NO: 5, and
at least one heavy chain (H) is selected from the group consisting of SEQ ID NO: 6, SEQ ID NO: 7 and SEQ ID NO: 8."

And insert:
--1. A monoclonal chimeric immunoglobulin comprising:
(i) two polypeptide chains, called heavy chains (H), of molecular weight from 40 kDa to 60 kDa, and
(ii) two polypeptide chains, called light chains (L), of molecular weight from 20 kDa to 30 kDa,
wherein each heavy chain (H) comprises:
a heavy chain variable region (VH) of a monoclonal antibody Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office* chosen from the group consisting of monoclonal antibodies specific to monomorphic epitopes of HLA class II antigens, and a heavy chain constant region (CH) of a human immunoglobulin chosen from the group consisting of IgAs, IgGs and IgMs, and wherein
at least one light chain (L) consists of the sequence SEQ ID NO: 5, and
at least one heavy chain (H) is selected from the group consisting of SEQ ID NO: 6, SEQ ID NO: 7 and SEQ ID NO: 8.--

SEQUENCE LISTING

<160> NUMBER OF SEQ ID NOS: 8

<210> SEQ ID NO 1
<211> LENGTH: 235
<212> TYPE: PRT
<213> ORGANISM: Artificial Sequence
<220> FEATURE:
<223> OTHER INFORMATION: Mouse/human chimeric sequence - Light chain
      Hu-IgG1 K [W6/32] - figure 9

<400> SEQUENCE: 1

Met Lys Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
            20                  25                  30

Val Ser Ala Gly Asp Arg Val Thr Ile Thr Cys Lys Ala Ser Gln Ser
        35                  40                  45

Val Ser Asn Asp Val Ala Trp Tyr Gln Gln Lys Pro Gly Gln Ser Pro
    50                  55                  60

Lys Leu Leu Ile Tyr Tyr Ala Ser Asn Arg Tyr Thr Gly Val Pro Asp
65                  70                  75                  80

```
Arg Phe Thr Gly Ser Gly Tyr Gly Thr Asp Phe Thr Phe Thr Ile Ser
                85              90                  95

Thr Val Gln Ala Glu Asp Leu Ala Val Tyr Phe Cys Gln Gln Asp Tyr
            100                 105                 110

Ser Ser Pro Pro Trp Thr Phe Gly Gly Gly Thr Lys Leu Glu Ile Arg
            115                 120                 125

Arg Thr Val Ala Ala Pro Ser Val Phe Ile Phe Pro Pro Ser Asp Glu
        130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
        210                 215                 220

Pro Val Thr Lys Ser Phe Asn Arg Gly Glu Cys
225                 230                 235

<210> SEQ ID NO 2
<211> LENGTH: 469
<212> TYPE: PRT
<213> ORGANISM: Artificial Sequence
<220> FEATURE:
<223> OTHER INFORMATION: Mouse/human chimeric sequence - Heavy chain
      Hu-IgG1 K [W6/32] - figure 10

<400> SEQUENCE: 2

Met Ala Val Leu Val Leu Leu Phe Cys Leu Val Thr Phe Pro Ser Cys
1               5                   10                  15

Val Leu Ser Gln Val Gln Leu Lys Gln Ser Gly Pro Gly Leu Val Gln
            20                  25                  30

Pro Ser Gln Ser Leu Ser Leu Thr Cys Thr Val Ser Gly Phe Ser Leu
        35                  40                  45

Thr Ser Tyr Gly Val His Trp Val Arg Gln Pro Pro Gly Lys Gly Leu
    50                  55                  60

Glu Trp Leu Gly Val Ile Trp Ser Gly Gly Ser Thr Asp Tyr Asn Ala
65                  70                  75                  80

Ala Phe Ile Ser Arg Leu Ser Ile Arg Lys Asp Asn Ser Lys Ser Gln
                85                  90                  95

Val Phe Phe Lys Met Asn Ser Leu Gln Ala Asp Asp Thr Ala Ile Tyr
            100                 105                 110

Tyr Cys Ala Arg Thr Phe Thr Thr Ser Thr Ser Ala Trp Phe Ala Tyr
        115                 120                 125

Trp Gly Gln Gly Thr Leu Val Thr Val Ser Ala Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205
```

```
Thr Val Pro Ser Ser Ser Leu Gly Thr Gln Thr Tyr Ile Cys Asn Val
    210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                    245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
        290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                    325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                    405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
        450                 455                 460

Leu Ser Pro Gly Lys
465

<210> SEQ ID NO 3
<211> LENGTH: 479
<212> TYPE: PRT
<213> ORGANISM: Artificial Sequence
<220> FEATURE:
<223> OTHER INFORMATION: Mouse/human chimeric sequence - Heavy chain
      Hu-IgA2 K [W6/32] - figure 11

<400> SEQUENCE: 3

Met Ala Val Leu Val Leu Phe Cys Leu Val Thr Phe Pro Ser Cys
1               5                   10                  15

Val Leu Ser Gln Val Gln Leu Lys Gln Ser Gly Pro Gly Leu Val Gln
            20                  25                  30

Pro Ser Gln Ser Leu Ser Leu Thr Cys Thr Val Ser Gly Phe Ser Leu
        35                  40                  45

Thr Ser Tyr Gly Val His Trp Val Arg Gln Pro Pro Gly Lys Gly Leu
    50                  55                  60

Glu Trp Leu Gly Val Ile Trp Ser Gly Gly Ser Thr Asp Tyr Asn Ala
65                  70                  75                  80

Ala Phe Ile Ser Arg Leu Ser Ile Arg Lys Asp Asn Ser Lys Ser Gln
```

```
                    85                  90                  95
Val Phe Phe Lys Met Asn Ser Leu Gln Ala Asp Asp Thr Ala Ile Tyr
            100                 105                 110
Tyr Cys Ala Arg Thr Phe Thr Thr Ser Thr Ser Ala Trp Phe Ala Tyr
            115                 120                 125
Trp Gly Gln Gly Thr Leu Val Thr Val Ser Ala Ala Ser Pro Thr Ser
            130                 135                 140
Pro Lys Val Phe Pro Leu Ser Leu Asp Ser Thr Pro Gln Asp Gly Asn
145                 150                 155                 160
Val Val Val Ala Cys Leu Val Gln Gly Phe Phe Pro Gln Glu Pro Leu
                165                 170                 175
Ser Val Thr Trp Ser Glu Ser Gly Gln Asn Val Thr Ala Arg Asn Phe
            180                 185                 190
Pro Pro Ser Gln Asp Ala Ser Gly Asp Leu Tyr Thr Thr Ser Ser Gln
            195                 200                 205
Leu Thr Leu Pro Ala Thr Gln Cys Pro Asp Gly Lys Ser Val Thr Cys
            210                 215                 220
His Val Lys His Tyr Thr Asn Pro Ser Gln Asp Val Thr Val Pro Cys
225                 230                 235                 240
Pro Val Pro Pro Pro Pro Cys Cys His Pro Arg Leu Ser Leu His
                245                 250                 255
Arg Pro Ala Leu Glu Asp Leu Leu Leu Gly Ser Glu Ala Asn Leu Thr
            260                 265                 270
Cys Thr Leu Thr Gly Leu Arg Asp Ala Ser Gly Ala Thr Phe Thr Trp
            275                 280                 285
Thr Pro Ser Ser Gly Lys Ser Ala Val Gln Gly Pro Pro Glu Arg Asp
            290                 295                 300
Leu Cys Gly Cys Tyr Ser Val Ser Ser Val Leu Pro Gly Cys Ala Gln
305                 310                 315                 320
Pro Trp Asn His Gly Glu Thr Phe Thr Cys Thr Ala Ala His Pro Glu
                325                 330                 335
Leu Lys Thr Pro Leu Thr Ala Asn Ile Thr Lys Ser Gly Asn Thr Phe
            340                 345                 350
Arg Pro Glu Val His Leu Leu Pro Pro Ser Glu Glu Leu Ala Leu
            355                 360                 365
Asn Glu Leu Val Thr Leu Thr Cys Leu Ala Arg Gly Phe Ser Pro Lys
            370                 375                 380
Asp Val Leu Val Arg Trp Leu Gln Gly Ser Gln Glu Leu Pro Arg Glu
385                 390                 395                 400
Lys Tyr Leu Thr Trp Ala Ser Arg Gln Glu Pro Ser Gln Gly Thr Thr
                405                 410                 415
Thr Phe Ala Val Thr Ser Ile Leu Arg Val Ala Ala Glu Asp Trp Lys
            420                 425                 430
Lys Gly Asp Thr Phe Ser Cys Met Val Gly His Glu Ala Leu Pro Leu
            435                 440                 445
Ala Phe Thr Gln Lys Thr Ile Asp Arg Leu Ala Gly Lys Pro Thr His
            450                 455                 460
Val Asn Val Ser Val Val Met Ala Glu Val Asp Gly Thr Cys Tyr
465                 470                 475
```

<210> SEQ ID NO 4
<211> LENGTH: 590
<212> TYPE: PRT
<213> ORGANISM: Artificial Sequence
<220> FEATURE:
<223> OTHER INFORMATION: Mouse/human chimeric sequence - Heavy chain
      Hu-IgM K [W6/32] - figure 12

<400> SEQUENCE: 4

```
Met Ala Val Leu Val Leu Leu Phe Cys Leu Val Thr Phe Pro Ser Cys
1               5                   10                  15

Val Leu Ser Gln Val Gln Leu Lys Gln Ser Gly Pro Gly Leu Val Gln
            20                  25                  30

Pro Ser Gln Ser Leu Ser Leu Thr Cys Thr Val Ser Gly Phe Ser Leu
        35                  40                  45

Thr Ser Tyr Gly Val His Trp Val Arg Gln Pro Pro Gly Lys Gly Leu
    50                  55                  60

Glu Trp Leu Gly Val Ile Trp Ser Gly Gly Ser Thr Asp Tyr Asn Ala
65                  70                  75                  80

Ala Phe Ile Ser Arg Leu Ser Ile Arg Lys Asp Asn Ser Lys Ser Gln
                85                  90                  95

Val Phe Phe Lys Met Asn Ser Leu Gln Ala Asp Asp Thr Ala Ile Tyr
            100                 105                 110

Tyr Cys Ala Arg Thr Phe Thr Thr Ser Thr Ser Ala Trp Phe Ala Tyr
        115                 120                 125

Trp Gly Gln Gly Thr Leu Val Thr Val Ser Ala Ala Ser Ala Pro Thr
    130                 135                 140

Leu Phe Pro Leu Val Ser Cys Glu Asn Ser Pro Ser Asp Thr Ser Ser
145                 150                 155                 160

Val Ala Val Gly Cys Leu Ala Gln Asp Phe Leu Pro Asp Ser Ile Thr
                165                 170                 175

Phe Ser Trp Lys Tyr Lys Asn Asn Ser Asp Ile Ser Ser Thr Arg Gly
            180                 185                 190

Phe Pro Ser Val Leu Arg Gly Gly Lys Tyr Ala Ala Thr Ser Gln Val
        195                 200                 205

Leu Leu Pro Ser Lys Asp Val Met Gln Gly Thr Asp Glu His Val Val
    210                 215                 220

Cys Lys Val Gln His Pro Asn Gly Asn Lys Glu Lys Asn Val Pro Leu
225                 230                 235                 240

Pro Val Ile Ala Glu Leu Pro Pro Lys Val Ser Val Phe Val Pro Pro
                245                 250                 255

Arg Asp Gly Phe Phe Gly Asn Pro Arg Lys Ser Lys Leu Ile Cys Gln
            260                 265                 270

Ala Thr Gly Phe Ser Pro Arg Gln Ile Gln Val Ser Trp Leu Arg Glu
        275                 280                 285

Gly Lys Gln Val Gly Ser Gly Val Thr Thr Asp Gln Val Gln Ala Glu
    290                 295                 300

Ala Lys Glu Ser Gly Pro Thr Thr Tyr Lys Val Thr Ser Thr Leu Thr
305                 310                 315                 320

Ile Lys Glu Ser Asp Trp Leu Ser Gln Ser Met Phe Thr Cys Arg Val
                325                 330                 335

Asp His Arg Gly Leu Thr Phe Gln Gln Asn Ala Ser Ser Met Cys Val
            340                 345                 350

Pro Asp Gln Asp Thr Ala Ile Arg Val Phe Ala Ile Pro Pro Ser Phe
        355                 360                 365

Ala Ser Ile Phe Leu Thr Lys Ser Thr Lys Leu Thr Cys Leu Val Thr
    370                 375                 380

Asp Leu Thr Thr Tyr Asp Ser Val Thr Ile Ser Trp Thr Arg Gln Asn
```

```
                385                 390                 395                 400
        Gly Glu Ala Val Lys Thr His Thr Asn Ile Ser Glu Ser His Pro Asn
                            405                 410                 415

Ala Thr Phe Ser Ala Val Gly Glu Ala Ser Ile Cys Glu Asp Asp Trp
                        420                 425                 430

Asn Ser Gly Glu Arg Phe Thr Cys Thr Val Thr His Thr Asp Leu Pro
                    435                 440                 445

Ser Pro Leu Lys Gln Thr Ile Ser Arg Pro Lys Gly Val Ala Leu His
                450                 455                 460

Arg Pro Asp Val Tyr Leu Leu Pro Pro Ala Arg Glu Gln Leu Asn Leu
        465                 470                 475                 480

Arg Glu Ser Ala Thr Ile Thr Cys Leu Val Thr Gly Phe Ser Pro Ala
                        485                 490                 495

Asp Val Phe Val Gln Trp Met Gln Arg Gly Gln Pro Leu Ser Pro Glu
                    500                 505                 510

Lys Tyr Val Thr Ser Ala Pro Met Pro Glu Pro Gln Ala Pro Gly Arg
                515                 520                 525

Tyr Phe Ala His Ser Ile Leu Thr Val Ser Glu Glu Trp Asn Thr
            530                 535                 540

Gly Glu Thr Tyr Thr Cys Val Val Ala His Glu Ala Leu Pro Asn Arg
        545                 550                 555                 560

Val Thr Glu Arg Thr Val Asp Lys Ser Thr Gly Lys Pro Thr Leu Tyr
                        565                 570                 575

Asn Val Ser Leu Val Met Ser Asp Thr Ala Gly Thr Cys Tyr
                    580                 585                 590

<210> SEQ ID NO 5
<211> LENGTH: 235
<212> TYPE: PRT
<213> ORGANISM: Artificial Sequence
<220> FEATURE:
<223> OTHER INFORMATION: Mouse/human chimeric sequence - Light chain
      Hu-IgG1 K [F3.3] - figure 13

<400> SEQUENCE: 5

Met Asp Phe Gln Val Gln Ile Phe Ser Phe Leu Leu Ile Ser Ala Ser
1               5                   10                  15

Val Ile Leu Ser Arg Gly Gln Ile Val Leu Thr Gln Ser Pro Ala Ile
                20                  25                  30

Met Ser Ala Ser Pro Gly Glu Lys Val Thr Met Thr Cys Ser Ala Ser
            35                  40                  45

Ser Ile Val Arg Tyr Met Tyr Trp Phe Gln Gln Lys Pro Gly Ser Ser
        50                  55                  60

Pro Arg Leu Leu Ile Tyr Asp Thr Ser Ser Leu Ser Gly Val Pro
65                  70                  75                  80

Val Arg Phe Ser Gly Ser Gly Ser Gly Thr Ser Tyr Ser Leu Thr Ile
                85                  90                  95

Ser Arg Met Glu Ala Glu Asp Ala Ala Thr Tyr Phe Cys Gln Gln Trp
            100                 105                 110

Ser Ser Tyr Pro Leu Thr Phe Gly Gly Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160
```

```
Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 6
<211> LENGTH: 477
<212> TYPE: PRT
<213> ORGANISM: Artificial Sequence
<220> FEATURE:
<223> OTHER INFORMATION: Mouse/human chimeric sequence - Heavy chain
      Hu-IgA2 K [F3.3] - figure 14

<400> SEQUENCE: 6

Met Asp Leu Arg Leu Ser Cys Ala Phe Ile Ile Val Leu Leu Lys Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Ser Trp Met Asn Trp Val Arg Gln Ser Pro Glu Lys Gly Leu
    50                  55                  60

Glu Trp Val Ala Glu Ile Arg Leu Lys Ser Asn Asn Tyr Ala Thr Arg
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Ser Glu Asp Thr
            100                 105                 110

Ala Ile Tyr Tyr Cys Thr Pro Leu Ser Tyr Ser Phe Asp Tyr Trp Gly
        115                 120                 125

Gln Gly Thr Thr Val Thr Val Ser Thr Ala Ser Pro Thr Ser Pro Lys
    130                 135                 140

Val Phe Pro Leu Ser Leu Asp Ser Thr Pro Gln Asp Gly Asn Val Val
145                 150                 155                 160

Val Ala Cys Leu Val Gln Gly Phe Phe Pro Gln Glu Pro Leu Ser Val
                165                 170                 175

Thr Trp Ser Glu Ser Gly Gln Asn Val Thr Ala Arg Asn Phe Pro Pro
            180                 185                 190

Ser Gln Asp Ala Ser Gly Asp Leu Tyr Thr Thr Ser Ser Gln Leu Thr
        195                 200                 205

Leu Pro Ala Thr Gln Cys Pro Asp Gly Lys Ser Val Thr Cys His Val
    210                 215                 220

Lys His Tyr Thr Asn Pro Ser Gln Asp Val Thr Val Pro Cys Pro Val
225                 230                 235                 240

Pro Pro Pro Pro Pro Cys Cys His Pro Arg Leu Ser Leu His Arg Pro
                245                 250                 255

Ala Leu Glu Asp Leu Leu Leu Gly Ser Glu Ala Asn Leu Thr Cys Thr
            260                 265                 270

Leu Thr Gly Leu Arg Asp Ala Ser Gly Ala Thr Phe Thr Trp Thr Pro
        275                 280                 285
```

```
Ser Ser Gly Lys Ser Ala Val Gln Gly Pro Pro Glu Arg Asp Leu Cys
    290                 295                 300

Gly Cys Tyr Ser Val Ser Ser Val Leu Pro Gly Cys Ala Gln Pro Trp
305                 310                 315                 320

Asn His Gly Glu Thr Phe Thr Cys Thr Ala Ala His Pro Glu Leu Lys
                325                 330                 335

Thr Pro Leu Thr Ala Asn Ile Thr Lys Ser Gly Asn Thr Phe Arg Pro
            340                 345                 350

Glu Val His Leu Leu Pro Pro Ser Glu Glu Leu Ala Leu Asn Glu
        355                 360                 365

Leu Val Thr Leu Thr Cys Leu Ala Arg Gly Phe Ser Pro Lys Asp Val
    370                 375                 380

Leu Val Arg Trp Leu Gln Gly Ser Gln Glu Leu Pro Arg Glu Lys Tyr
385                 390                 395                 400

Leu Thr Trp Ala Ser Arg Gln Glu Pro Ser Gln Gly Thr Thr Thr Phe
                405                 410                 415

Ala Val Thr Ser Ile Leu Arg Val Ala Ala Glu Asp Trp Lys Lys Gly
            420                 425                 430

Asp Thr Phe Ser Cys Met Val Gly His Glu Ala Leu Pro Leu Ala Phe
        435                 440                 445

Thr Gln Lys Thr Ile Asp Arg Leu Ala Gly Lys Pro Thr His Val Asn
    450                 455                 460

Val Ser Val Val Met Ala Glu Val Asp Gly Thr Cys Tyr
465                 470                 475

<210> SEQ ID NO 7
<211> LENGTH: 467
<212> TYPE: PRT
<213> ORGANISM: Artificial Sequence
<220> FEATURE:
<223> OTHER INFORMATION: Mouse/human chimeric sequence - Heavy chain
      Hu-IgG1 K [F3.3] - figure 15

<400> SEQUENCE: 7

Met Asp Leu Arg Leu Ser Cys Ala Phe Ile Ile Val Leu Leu Lys Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Ser Trp Met Asn Trp Val Arg Gln Ser Pro Glu Lys Gly Leu
    50                  55                  60

Glu Trp Val Ala Glu Ile Arg Leu Lys Ser Asn Asn Tyr Ala Thr Arg
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Ser Glu Asp Thr
            100                 105                 110

Ala Ile Tyr Tyr Cys Thr Pro Leu Ser Tyr Ser Phe Asp Tyr Trp Gly
        115                 120                 125

Gln Gly Thr Thr Val Thr Val Ser Thr Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
```

```
                165                 170                 175
Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
        260                 265                 270

Ile Ser Arg Thr Pro Glu Val Thr Cys Val Val Val Asp Val Ser His
    275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
        340                 345                 350

Glu Lys Thr Ile Ser Lys Ala Lys Gly Gln Pro Arg Glu Pro Gln Val
    355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
    435                 440                 445

His Glu Ala Leu His Asn His Tyr Thr Gln Lys Ser Leu Ser Leu Ser
    450                 455                 460

Pro Gly Lys
465

<210> SEQ ID NO 8
<211> LENGTH: 588
<212> TYPE: PRT
<213> ORGANISM: Artificial Sequence
<220> FEATURE:
<223> OTHER INFORMATION: Mouse/human chimeric sequence - Heavy chain
      Hu-IgM K [F3.3] - figure 16

<400> SEQUENCE: 8

Met Asp Leu Arg Leu Ser Cys Ala Phe Ile Ile Val Leu Leu Lys Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45
```

```
Ser Asn Ser Trp Met Asn Trp Val Arg Gln Ser Pro Glu Lys Gly Leu
    50              55                  60

Glu Trp Val Ala Glu Ile Arg Leu Lys Ser Asn Asn Tyr Ala Thr Arg
65              70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Ser Glu Asp Thr
            100                 105                 110

Ala Ile Tyr Tyr Cys Thr Pro Leu Ser Tyr Ser Phe Asp Tyr Trp Gly
        115                 120                 125

Gln Gly Thr Thr Val Thr Val Ser Thr Ala Ser Ala Pro Thr Leu Phe
130                 135                 140

Pro Leu Val Ser Cys Glu Asn Ser Pro Ser Asp Thr Ser Ser Val Ala
145                 150                 155                 160

Val Gly Cys Leu Ala Gln Asp Phe Leu Pro Asp Ser Ile Thr Phe Ser
                165                 170                 175

Trp Lys Tyr Lys Asn Asn Ser Asp Ile Ser Ser Thr Arg Gly Phe Pro
            180                 185                 190

Ser Val Leu Arg Gly Gly Lys Tyr Ala Ala Thr Ser Gln Val Leu Leu
        195                 200                 205

Pro Ser Lys Asp Val Met Gln Gly Thr Asp Glu His Val Val Cys Lys
210                 215                 220

Val Gln His Pro Asn Gly Asn Lys Glu Lys Asn Val Pro Leu Pro Val
225                 230                 235                 240

Ile Ala Glu Leu Pro Pro Lys Val Ser Val Phe Val Pro Pro Arg Asp
                245                 250                 255

Gly Phe Phe Gly Asn Pro Arg Lys Ser Lys Leu Ile Cys Gln Ala Thr
            260                 265                 270

Gly Phe Ser Pro Arg Gln Ile Gln Val Ser Trp Leu Arg Glu Gly Lys
        275                 280                 285

Gln Val Gly Ser Gly Val Thr Thr Asp Gln Val Gln Ala Glu Ala Lys
290                 295                 300

Glu Ser Gly Pro Thr Thr Tyr Lys Val Thr Ser Thr Leu Thr Ile Lys
305                 310                 315                 320

Glu Ser Asp Trp Leu Ser Gln Ser Met Phe Thr Cys Arg Val Asp His
                325                 330                 335

Arg Gly Leu Thr Phe Gln Gln Asn Ala Ser Ser Met Cys Val Pro Asp
            340                 345                 350

Gln Asp Thr Ala Ile Arg Val Phe Ala Ile Pro Pro Ser Phe Ala Ser
        355                 360                 365

Ile Phe Leu Thr Lys Ser Thr Lys Leu Thr Cys Leu Val Thr Asp Leu
370                 375                 380

Thr Thr Tyr Asp Ser Val Thr Ile Ser Trp Thr Arg Gln Asn Gly Glu
385                 390                 395                 400

Ala Val Lys Thr His Thr Asn Ile Ser Glu Ser His Pro Asn Ala Thr
                405                 410                 415

Phe Ser Ala Val Gly Glu Ala Ser Ile Cys Glu Asp Asp Trp Asn Ser
            420                 425                 430

Gly Glu Arg Phe Thr Cys Thr Val Thr His Thr Asp Leu Pro Ser Pro
        435                 440                 445

Leu Lys Gln Thr Ile Ser Arg Pro Lys Gly Val Ala Leu His Arg Pro
450                 455                 460

Asp Val Tyr Leu Leu Pro Pro Ala Arg Glu Gln Leu Asn Leu Arg Glu
```

-continued

```
            465                 470                 475                 480

Ser Ala Thr Ile Thr Cys Leu Val Thr Gly Phe Ser Pro Ala Asp Val
                        485                 490                 495

Phe Val Gln Trp Met Gln Arg Gly Gln Pro Leu Ser Pro Glu Lys Tyr
                        500                 505                 510

Val Thr Ser Ala Pro Met Pro Glu Pro Gln Ala Pro Gly Arg Tyr Phe
                        515                 520                 525

Ala His Ser Ile Leu Thr Val Ser Glu Glu Glu Trp Asn Thr Gly Glu
                        530                 535                 540

Thr Tyr Thr Cys Val Val Ala His Glu Ala Leu Pro Asn Arg Val Thr
        545                 550                 555                 560

Glu Arg Thr Val Asp Lys Ser Thr Gly Lys Pro Thr Leu Tyr Asn Val
                        565                 570                 575

Ser Leu Val Met Ser Asp Thr Ala Gly Thr Cys Tyr
                        580                 585
```